(12) United States Patent
Chen et al.

(10) Patent No.: US 10,058,256 B2
(45) Date of Patent: Aug. 28, 2018

(54) MULTI-SPECTRAL LASER IMAGING (MSLI) METHODS AND SYSTEMS FOR BLOOD FLOW AND PERFUSION IMAGING AND QUANTIFICATION

(71) Applicant: East Carolina University, Greenville, NC (US)

(72) Inventors: Cheng Chen, Greenville, NC (US); T. Bruce Ferguson, Jr., Raleigh, NC (US); Zhiyong Peng, Greenville, NC (US); Kenneth Michael Jacobs, Greenville, NC (US)

(73) Assignee: East Carolina University, Greenville, NC (US)

( * ) Notice: Subject to any disclaimer, the term of this patent is extended or adjusted under 35 U.S.C. 154(b) by 0 days.

(21) Appl. No.: 15/054,830

(22) Filed: Feb. 26, 2016

(65) Prior Publication Data

US 2016/0270672 A1 Sep. 22, 2016

Related U.S. Application Data

(60) Provisional application No. 62/136,010, filed on Mar. 20, 2015.

(51) Int. Cl.
*A61B 5/02* (2006.01)
*A61B 5/026* (2006.01)
*A61B 5/00* (2006.01)

(52) U.S. Cl.
CPC .......... *A61B 5/0261* (2013.01); *A61B 5/0077* (2013.01); *A61B 5/721* (2013.01);
(Continued)

(58) Field of Classification Search
CPC ..... A61B 5/0086; A61B 5/0261; A61B 5/145; A61B 5/7207; A61B 5/0077; A61B 8/06
See application file for complete search history.

(56) References Cited

U.S. PATENT DOCUMENTS 4,541,433 A 9/1985 Baudino
5,058,596 A 10/1991 Makino et al.
(Continued)

FOREIGN PATENT DOCUMENTS

JP 10-290791 11/1998
JP 2005-118325 5/2005
(Continued)

OTHER PUBLICATIONS

Notification of Transmittal of the International Search Report and the Written Opinion of the International Searching Authority, or the Declaration, PCT/US2016/020201, dated Jul. 27, 2016, 12 pages.
(Continued)

*Primary Examiner* — Catherine Voorhees
*Assistant Examiner* — Natasha Patel
(74) *Attorney, Agent, or Firm* — Myers Bigel, P.A.

(57) ABSTRACT

Some embodiments of the present inventive concept provide a system that uses two wavelengths of differential transmittance through a sample to apply laser speckle or laser Doppler imaging. A first of the two wavelengths is within the visible range that has zero or very shallow penetration. This wavelength captures the anatomical structure of tissue/organ surface and serves as a position marker of the sample but not the subsurface movement of blood flow and perfusion. A second wavelength is in the near Infra-Red (NIR) range, which has much deeper penetration. This wavelength reveals the underlying blood flow physiology and correlates both to the motion of the sample and also the movement of blood flow and perfusion. Thus, true motion of blood flow and perfusion can be derived from the NIR imaging measurement without being affected by the motion artifact of the target.

23 Claims, 19 Drawing Sheets

(52) U.S. Cl.
CPC .......... *A61B 5/7207* (2013.01); *A61B 5/7271* (2013.01); *A61B 2576/00* (2013.01)

(56) References Cited

U.S. PATENT DOCUMENTS

| | | | |
|---|---|---|---|
| 5,074,307 A | 12/1991 | Aizu et al. | |
| 5,129,400 A | 7/1992 | Makino et al. | |
| 5,161,531 A | 11/1992 | Parsons et al. | |
| 5,240,006 A | 8/1993 | Fujii et al. | |
| 5,291,885 A | 3/1994 | Taniji et al. | |
| 5,291,886 A | 3/1994 | Katayama et al. | |
| 5,490,505 A | 2/1996 | Diab et al. | |
| 5,588,436 A | 12/1996 | Narayanan et al. | |
| 5,692,510 A | 12/1997 | Gordon et al. | |
| 5,860,922 A | 1/1999 | Gordon et al. | |
| 6,045,511 A | 4/2000 | Ott et al. | |
| 6,263,227 B1 | 7/2001 | Boggett et al. | |
| 6,537,223 B1 | 3/2003 | Kristiansen | |
| 6,587,701 B1 | 7/2003 | Stranc et al. | |
| 6,631,286 B2 | 10/2003 | Pfeiffer et al. | |
| 6,671,540 B1* | 12/2003 | Hochman | A61B 5/0059 600/431 |
| 6,766,188 B2 | 7/2004 | Soller | |
| 6,915,154 B1 | 7/2005 | Docherty et al. | |
| 6,944,494 B2 | 9/2005 | Forrester et al. | |
| 6,974,416 B2 | 12/2005 | Booker et al. | |
| 7,031,504 B1 | 4/2006 | Argiro et al. | |
| 7,096,058 B2 | 8/2006 | Miyahara et al. | |
| 7,113,817 B1 | 9/2006 | Winchester, Jr. et al. | |
| 7,200,431 B2 | 4/2007 | Franco et al. | |
| 7,231,243 B2 | 6/2007 | Tearney et al. | |
| 7,270,637 B2 | 9/2007 | Shin | |
| 7,309,313 B2 | 12/2007 | Nakata et al. | |
| 7,404,640 B2 | 7/2008 | Ferguson et al. | |
| 7,468,039 B2 | 12/2008 | Lui | |
| 7,496,395 B2 | 2/2009 | Serov et al. | |
| 7,541,602 B2 | 6/2009 | Metzger et al. | |
| 7,542,790 B2 | 6/2009 | Jensen et al. | |
| 7,809,225 B2 | 10/2010 | Bouma et al. | |
| 7,809,226 B2 | 10/2010 | Bouma et al. | |
| 9,226,673 B2 | 1/2016 | Ferguson, Jr. et al. | |
| 9,271,658 B2 | 3/2016 | Ferguson, Jr. et al. | |
| 2002/0016533 A1* | 2/2002 | Marchitto | A61B 5/0066 600/310 |
| 2002/0173723 A1 | 11/2002 | Lewis et al. | |
| 2003/0225328 A1 | 12/2003 | DeMeester et al. | |
| 2003/0231511 A1 | 12/2003 | Thibault | |
| 2005/0046969 A1 | 3/2005 | Beatson et al. | |
| 2006/0058662 A1 | 3/2006 | Kobayashi et al. | |
| 2006/0241460 A1 | 10/2006 | Kimura et al. | |
| 2006/0291708 A1 | 12/2006 | Dehmeshki et al. | |
| 2007/0008615 A1 | 1/2007 | Miyawaki et al. | |
| 2007/0109784 A1 | 5/2007 | Kosnick et al. | |
| 2007/0203413 A1 | 8/2007 | Frangioni | |
| 2008/0049268 A1 | 2/2008 | Hardy et al. | |
| 2008/0071176 A1 | 3/2008 | Docherty et al. | |
| 2008/0107361 A1 | 5/2008 | Asukai et al. | |
| 2008/0132794 A1 | 6/2008 | Alfano et al. | |
| 2008/0188726 A1 | 8/2008 | Presura et al. | |
| 2008/0262359 A1 | 10/2008 | Tearney et al. | |
| 2009/0041201 A1 | 2/2009 | Wang et al. | |
| 2009/0118623 A1 | 5/2009 | Serov et al. | |
| 2009/0177098 A1 | 7/2009 | Yakubo et al. | |
| 2009/0209834 A1 | 8/2009 | Fine | |
| 2009/0214098 A1 | 8/2009 | Hornegger et al. | |
| 2009/0216098 A1 | 8/2009 | Stranc et al. | |
| 2010/0056936 A1 | 3/2010 | Fujii et al. | |
| 2010/0067767 A1 | 3/2010 | Arakita et al. | |
| 2010/0069759 A1 | 3/2010 | Schuhrke et al. | |
| 2010/0168585 A1 | 7/2010 | Fujii et al. | |
| 2010/0172567 A1* | 7/2010 | Prokoski | A61B 5/0064 382/132 |
| 2010/0209002 A1 | 8/2010 | Thiel et al. | |
| 2010/0284693 A1 | 11/2010 | Agmon et al. | |
| 2010/0305454 A1 | 12/2010 | Dvorsky et al. | |
| 2011/0013002 A1 | 1/2011 | Thompson et al. | |
| 2011/0068007 A1 | 3/2011 | Pang et al. | |
| 2011/0071382 A1 | 3/2011 | Miyazaki et al. | |
| 2011/0137169 A1 | 6/2011 | Akaki et al. | |
| 2011/0164035 A1 | 7/2011 | Liao et al. | |
| 2011/0169978 A1 | 7/2011 | Lasser et al. | |
| 2011/0319775 A1 | 12/2011 | Fujii et al. | |
| 2012/0071769 A1 | 3/2012 | Dunn et al. | |
| 2012/0078113 A1 | 3/2012 | Hitestone et al. | |
| 2012/0095354 A1 | 4/2012 | Dunn et al. | |
| 2012/0108956 A1 | 5/2012 | Warger, II et al. | |
| 2012/0191005 A1 | 7/2012 | Sobol et al. | |
| 2012/0277559 A1* | 11/2012 | Kohl-Bareis | A61B 5/0261 600/324 |
| 2014/0003740 A1 | 1/2014 | Bone | |
| 2014/0187966 A1 | 7/2014 | Theirman | |
| 2014/0276097 A1 | 9/2014 | Sharonov | |
| 2014/0293091 A1* | 10/2014 | Rhoads | G01J 3/513 348/234 |
| 2014/0340482 A1 | 11/2014 | Kanarowski | |
| 2016/0198961 A1* | 7/2016 | Homyk | A61B 5/0082 600/476 |
| 2017/0091962 A1 | 3/2017 | Hagiwara | |
| 2017/0270379 A1 | 9/2017 | Kasai et al. | |

FOREIGN PATENT DOCUMENTS

| | | |
|---|---|---|
| JP | 2008-139543 | 6/2008 |
| WO | WO 2006/021096 A1 | 3/2006 |
| WO | WO 2006/116672 A2 | 11/2006 |
| WO | WO 2009/127972 A2 | 10/2009 |
| WO | WO 2010/131550 A1 | 11/2010 |
| WO | WO 2012/096878 A2 | 7/2012 |
| WO | WO 2013/190391 A2 | 12/2013 |
| WO | WO 2014/006465 A1 | 1/2014 |
| WO | WO 2014/009859 A2 | 1/2014 |
| WO | WO 2016/061041 A1 | 4/2016 |
| WO | WO 2016/061052 A1 | 4/2016 |

OTHER PUBLICATIONS

U.S. Appl. No. 15/518,545, Chen et al., filed Apr. 12, 2017.
U.S. Appl. No. 15/518,548, Chen et al., filed Apr. 12, 2017.
Aizu, Y et al. (1991) "Bio-Speckle Phenomena and Their Application to the Evaluation of Blood Flow" Optics and Laser Technology, vol. 23, No. 4, Aug. 1, 1991.
Brezinski, M. E., G. J. Tearney, et al. (1996). "Imaging of coronary artery microstructure (in vitro) with optical coherence tomography." American Journal of Cardiology 77 (1): 92-93.
Briers et al., (1995) "Quasi real-time digital version of single-exposure speckle photography for full-field monitoring of velocity or flow fields," Optics Communications 116: 36-42.
Briers, J. David, (2001) "Laser Doppler, speckle and related techniques for blood perfusion mapping and imaging," Physiol. Meas. 22: R35-R66.
Chen, Z. P., T. E. Milner, et al. (1997). "Noninvasive imaging of in vivo blood flow velocity using optical Doppler tomography." Optics Letters 22(14): 1119-1121.
Cheng et al., (2004) "Laser speckle imaging of blood flow in microcirculation," Phys. Med. Biol., 49: 1347-1357.
Choi et al., "Linear response range characterization and in vivo application of laser speckle imaging of blood flow dynamics," Journal of Biomedical Optics, Jul./Aug. 2006, 11(4): 041129.
Cioffi, G. A. (2001). "Three common assumptions about ocular blood flow and glaucoma." Survey of Ophthalmology 45: S325-S331.
Draijer, Matthijs J., "High Speed Perfusion Imaging Based on Laser Speckle Fluctuations," Printed by Ridderprint, Ridderkerk, The Netherlands 2010, 145 pages.
Draijer et al., "Twente Optical Perfusion Camera: system overview and performance for video rate laser Doppler perfusion imaging," Optics Express, Mar. 2, 2009, 17(5): 3211-3225.
Duncan et al., "Can laser speckle flowmetry be made a quantitative tool?," J. Opt. Soc. Am. A, Aug. 2008, 24(8): 2088-2094.

(56) References Cited

OTHER PUBLICATIONS

Dunn et al. "Dynamic imaging of cerebral blood flow using laser speckle", J. of Cerebral Blood Flow and Metabolism 21, 195-201 (2001).
Dunn et al., (2011) A Transmissive Laser Speckle Imaging Technique for Measuring Deep Tissue Blood Flow: An Example Application in Finger Joints, Lasers in Surgery and Medicine, 43: 21-28.
Eun, H. C. (1995). "Evaluation of skin blood flow by laser Doppler flowmetry. [Review] [151 refs]." Clinics in Dermatology 13(4): 337-47.
Fercher et al., "Flow Visualization by Means of Single-Exposure Speckle Photography," Optics Communications, Jun. 1, 1981, 37(5): 326-330.
Gandjbakhche, A. H., P. Mills, et al. (1994). "Light-Scattering Technique for the Study of Orientation and Deformation of Red-Blood-Cells in a Concentrated Suspension." Applied Optics 33(6): 1070-1078.
Izatt, J. A., M. D. Kulkarni, et al. (1996). "Optical coherence tomography and microscopy in gastrointestinal tissues." IEEE Journal of Selected Topics in Quantum Electronics 2(4): 1017.
Jang, I. K., G. J. Tearney, et al. (2001). "Visualization of Tissue Prolapse Between Coronary Stent Struts by Optical Coherence Tomography: Comparison With Intravascular Ultrasound." Images in Cardiovascular Medicine, American Heart Association, http://circ.ahajournals.org/content, p. 2754.
Konishi and Fujii "Real-time visualization of retinal microcirculation by laser flowgraphy", Opt. Eng. 34, 753-757 (1995).
Kruijt et al., (2006), "Laser speckle imaging of dynamic changes in flow during photodynamic therapy," Lasers Med Sci, 21: 208-212.
Leitgeb, R. A., L. Schmetterer, et al. (2003). "Real-time assessment of retinal blood flow with ultrafast acquisition by color Doppler Fourier domain optical coherence tomography." Optics Express 11(23): 3116-3121.
Lesnick et al., "New Generation Optical Would Monitoring Device," CW Optics, Inc., Yorktown, Virginia, USA, Admitted Prior Art, 1 page.
Li et al., "Imaging cerebral blood flow through the intact rate skull with temporal laser speckle imaging," Optics Letters, Jun. 15, 2006, 31(12): 1824-1826.
Matsievskii, D.D., (2004) "Blood Flow Measurements in Studies of Macro- and Microcirculation," Bulletin of Experimental Biology and Medicine, 6: 541-544.
Nadkarni, Seemantini K. et al (2005) "Characterization of Atherosclerotic Plaques by Laser Speckle Imaging" Circulation vol. 112, pp. 885-892.
Nelson, J. S., K. M. Kelly, et al. (2001). "Imaging blood flow in human port-wine stain in situ and in real time using optical Doppler tomography." Archives of Dermatology 137(6): 741-744.
Ohtsubo et al., (1976) "Velocity measurement of a diffuse object by using time-varying speckles," Optical and Quantum Electronics, 8: 523-529.
Oshima, M., R. Torii, et al. (2001). "Finite element simulation of blood flow in the cerebral artery." Computer Methods in Applied Mechanics and Engineering 191 (6-7): 661-671.
Parthasarathy et al., "Laser speckle contrast imaging of cerebral blood flow in humans during neurosurgery: a pilot clinical study," Journal of Biomedical Optics, 15(6) Nov./Dec. 2010, pp. 066030-1 to 066030-8.
Rege et al., "Multiexposure laser speckle contrast imaging of the angiogenic microenvironment," Journal of Biomedical Optics, 16(5), May 2011, pp. 056006-1 to 056006-10.
Ren, Hongwu et al., "Phase-Resolved Functional Optical Coherence Tomography: Simultaneous Imaging of in Situ Tissue Structure, Blood Flow Velocity, Standard Deviation, Birefringence, and Stokes Vectors in Human Skin," Optics Letters, vol. 27, No. 19, Oct. 1, 2002, pp. 1702-1704.
Richards G.J. et al. (1997) "Laser Speckle Contrast Analysis (LASCA): A Technique for Measuring Capillary Blood Flow Using the First Order Statistics of Laser Speckle Patterns" Apr. 2, 1997.
Ruth, B. "blood flow determination by the laser speckle method", Int J Microcirc: Clin Exp, 1990, 9:21-45.
Ruth, et al., (1993) "Noncontact Determination of Skin Blood Flow Using the Laser Speckle Method: Application to Patients with Peripheral Arterial Occlusive Disease (PAOD) and to Type-I Diabetes," Lasers in Surgery and Medicine 13: 179-188.
Subhash, Hrebesh M., "Biophotonics Modalities for High-Resolution Imaging of Microcirculatory Tissue Beds Using Endogenous Contrast: A Review of Present Scenario and Prospects," International Journal of Optics, vol. 2011, Article ID 293684, 20 pages.
Tearney et al., "Atherosclerotic plaque characterization by spatial and temporal speckle pattern analysis", CLEO 2001, vol. 56, pp. 307-307.
Wang, X. J., T. E. Milner, et al. (1997). "Measurement of fluid-flow-velocity profile in turbid media by the use of optical Doppler tomography." Applied Optics 36(1): 144-149.
Wardell et al., "ECG—Triggering of the Laser Doppler Perfusion Imaging Signal," Proceedings of the 20$^{th}$ Annual International Conference of the IEEE Engineering in Medicine and Biology Sociiety, vol. 20, No. 4, 1998, pp. 1879-1880.
Weber et al., (2004) "Optical imaging of the spatiotemporal dynamics of cerebral blood flow and oxidative metabolism in the rat barrel cortex," European Journal of Neuroscience, 20: 2664-2670.
White, Brian R. et al., "In Vivo Dynamic Human Retinal Blood Flow Imaging Using Ultra-High-Speed Spectral Domain Optical Doppler Tomography," Optics Express, Dec. 15, 2003, 11(25): 3490-3497.
Wussling et al., "Laser diffraction and speckling studies in skeletal and heart muscle", Biomed, Biochem, Acta, 1986, 45(1/2):S 23-S 27.
Yazdanfar et al., "In Vivo imaging in blood flow in human retinal vessels using color Doppler optical coherence tomography", SPIE, 1999 vol. 3598, pp. 177-184.
Yazdanfar, S., A. M. Rollins, et al. (2000). "Imaging and velocimetry of human retinal circulation with color Doppler optical coherence tomography." Optics Letters, vol. 25, No. 19, Oct. 1, 2000, pp. 1448-1450.
Yazdanfar, S., A. M. Rollins, et al. (2003). "In vivo imaging of human retinal flow dynamics by color Doppler optical coherence tomography." Archives of Ophthalmology 121(2): 235-239.
Zakharov et al., "Dynamic laser speckle imaging of cerebral blood flow," Optics Express, vol. 17, No. 16, Aug. 3, 2009, pp. 13904-13917.
Zakharov et al., "Quantitative modeling of laser speckle imaging," Optics Letters, Dec. 1, 2006; 31(23): 3465-3467.
Zhao, Y. H., Z. P. Chen, et al. (2000). "Doppler standard deviation imaging for clinical monitoring of in vivo human skin blood flow." Optics Letters 25(18): 1358-1360.
U.S. Appl. No. 15/559,605, filed Sep. 19, 2017, Peng et al.
U.S. Appl. No. 15/559,646, filed Sep. 19, 2017, Peng et al.
Furstenberg et al. "Laser speckle reduction techniques for mid-infrared microscopy and stand-off spectroscopy" *Proceedings of SPIE* 10210:1021004-1-8 (2017).
Redding et al. "Speckle-free laser imaging using random laser illumination" *Nature Photonics* 6:355-359 (2012).
Ren et al. "A simultaneous multimodal imaging system for tissue functional parameters" *Proceedings of SPIE* 8937:893706-1-12 (2014).
Zhang et al. "Multimodal imaging of ischemic wounds" *Proceedings of SPIE* 8553:85531G1-8 (2012).

\* cited by examiner

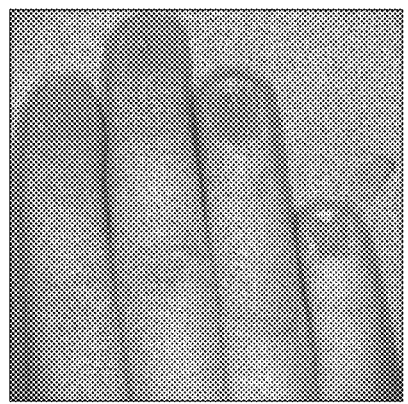
FIG. 7A
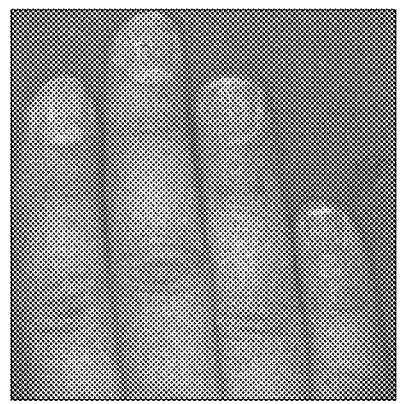
FIG. 7B
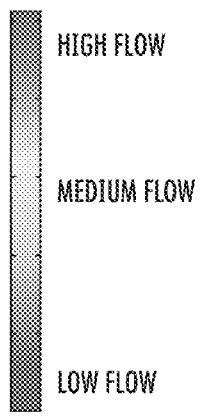
HIGH FLOW
MEDIUM FLOW
LOW FLOW

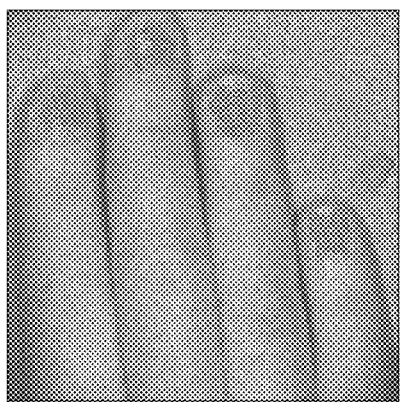
FIG. 8A
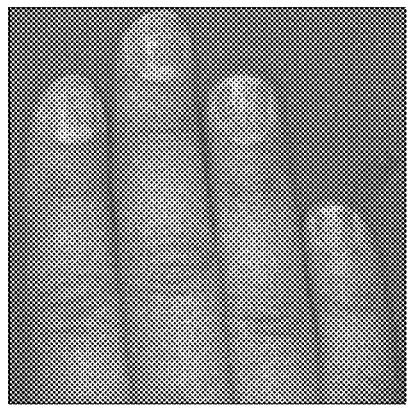
FIG. 8B
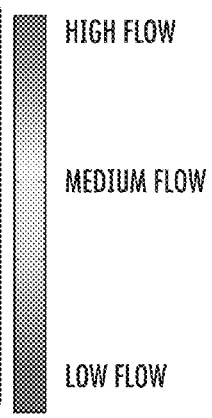
HIGH FLOW
MEDIUM FLOW
LOW FLOW

PANEL A

950

PANEL B

950

FIG. 10A
FIG. 10B
PANEL A
PANEL B
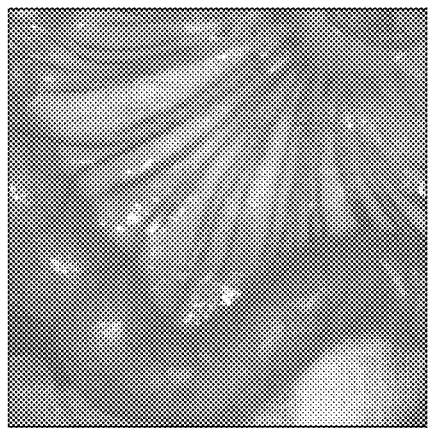
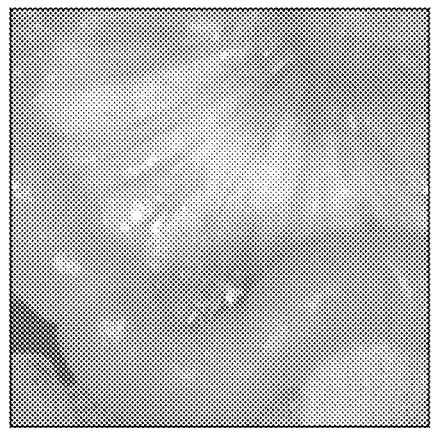
PANEL C
PANEL D (A+B+C)
HIGH FLOW
MEDIUM FLOW
LOW FLOW
FIG. 10C
FIG. 10D FIG. 11A
PANEL A
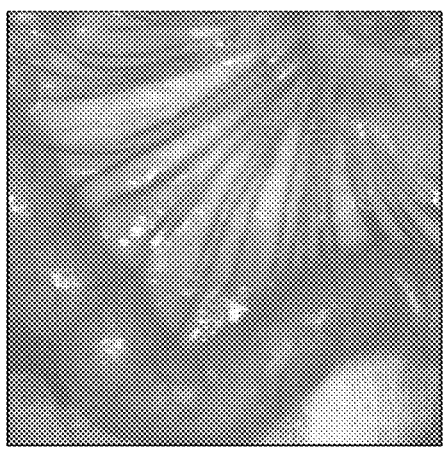
PANEL B
PANEL C (A ADJUSTS BRIGHTNESS AND B ADJUSTS COLOR)
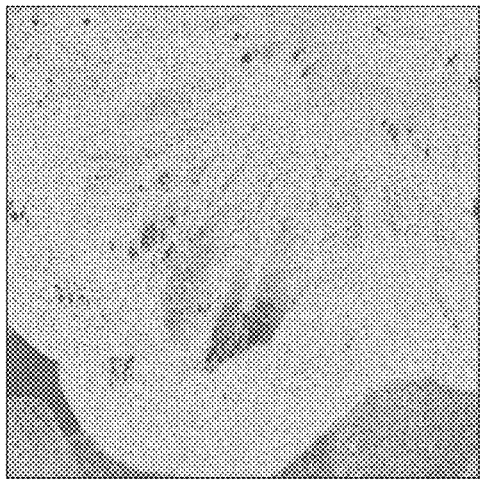
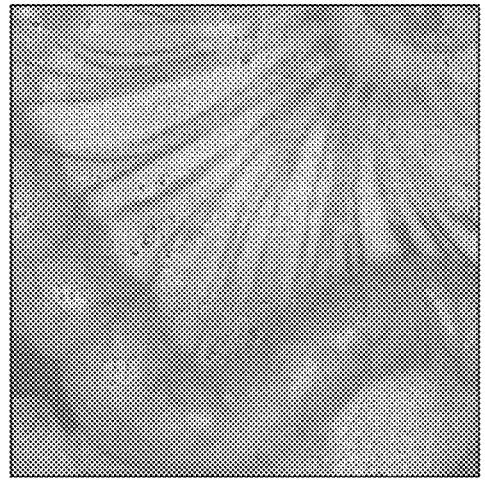
FIG. 11B
FIG. 11C FIG. 12A
PANEL A
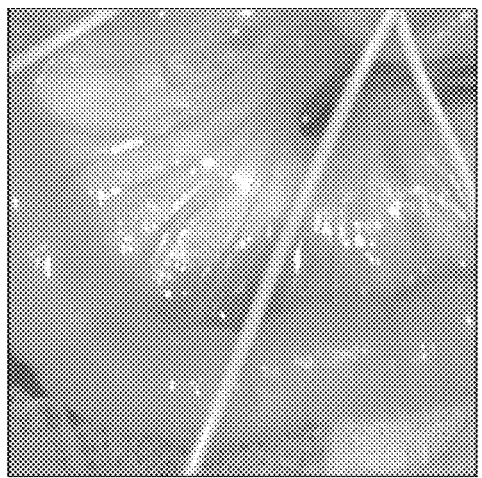
FIG. 12B
PANEL B
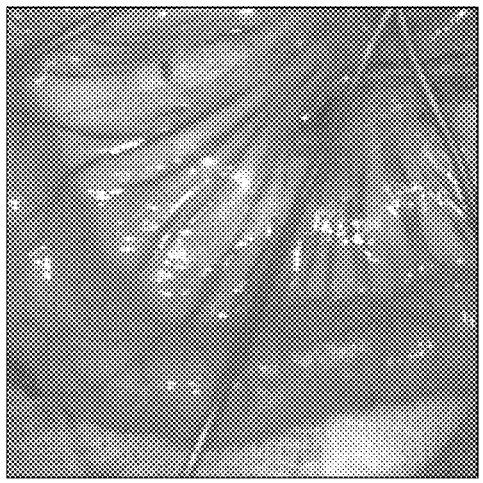
PANEL C
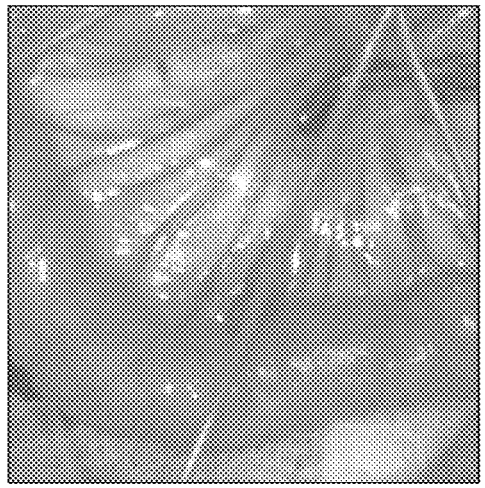
FIG. 12C
PANEL D
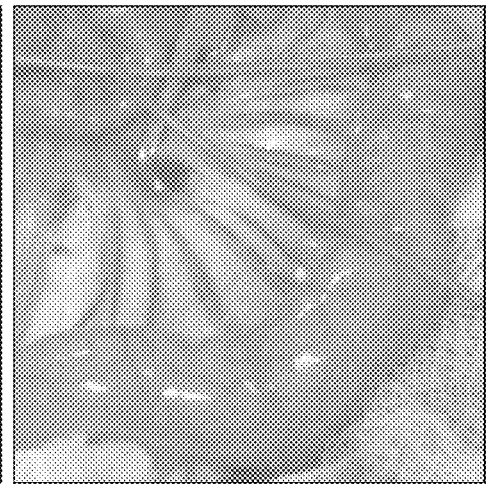
FIG. 12D FIG. 13A
PANEL A
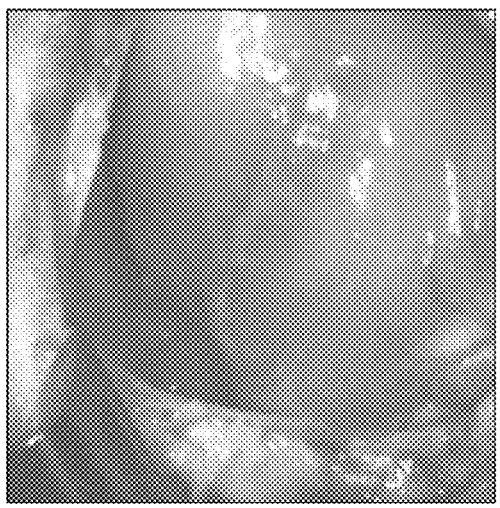
FIG. 13B
PANEL B
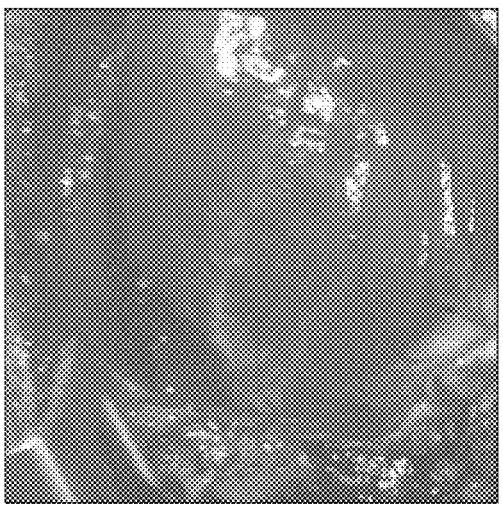
PANEL C
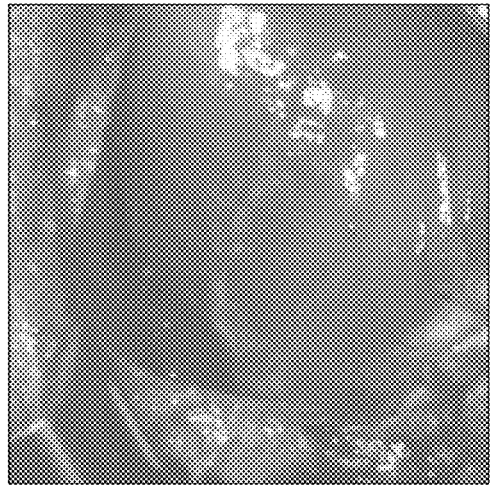
FIG. 13C
PANEL D
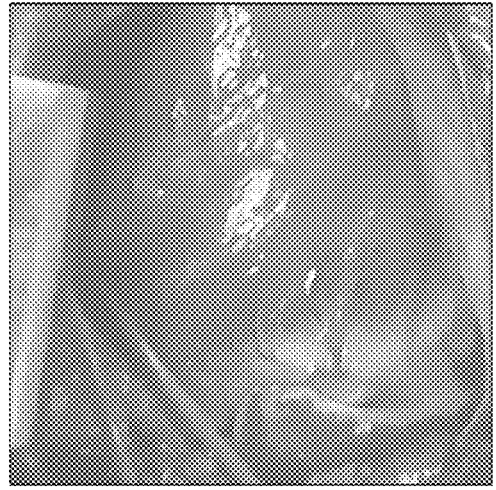
FIG. 13D FIG. 14E
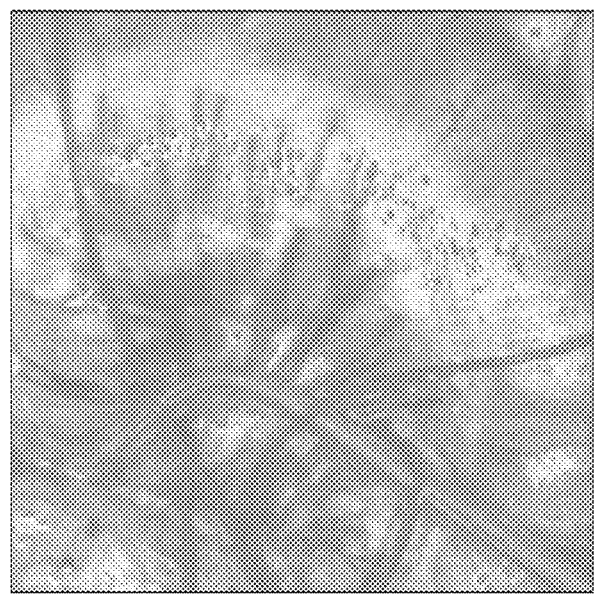
FIG. 15A
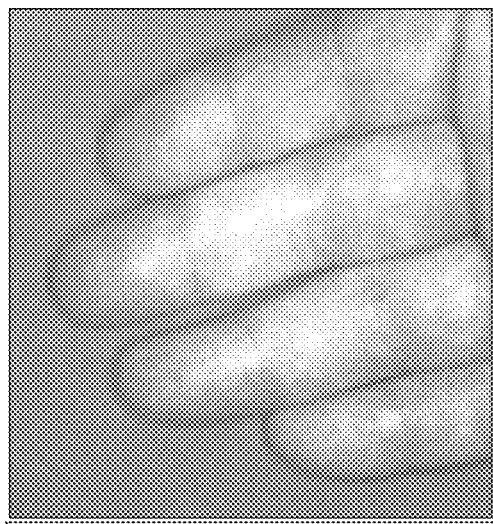
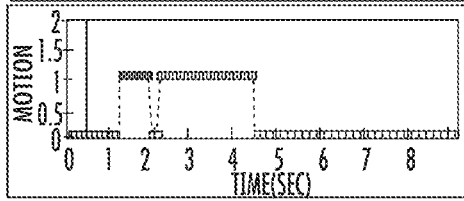
FIG. 15B
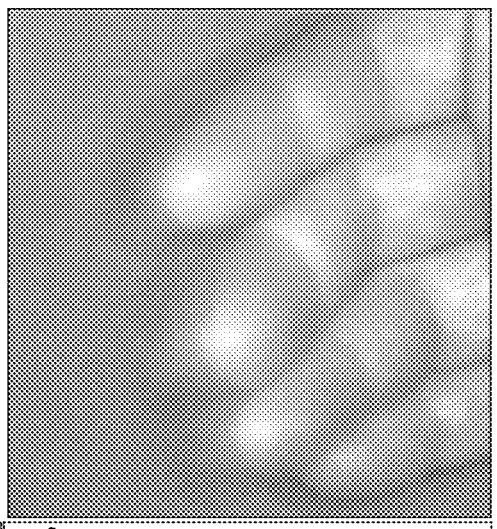
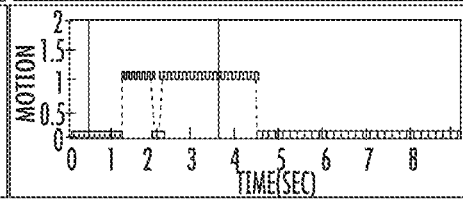

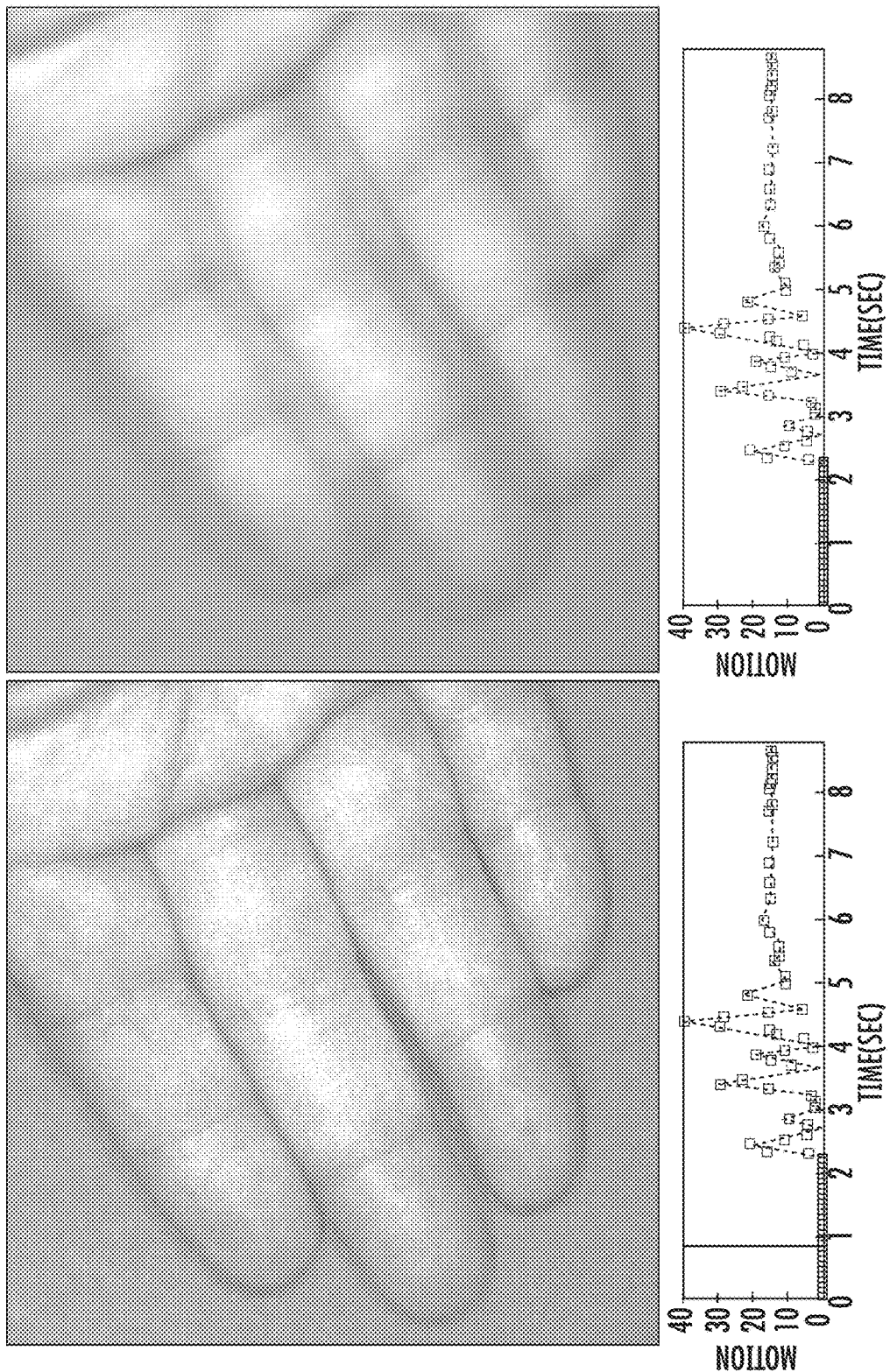

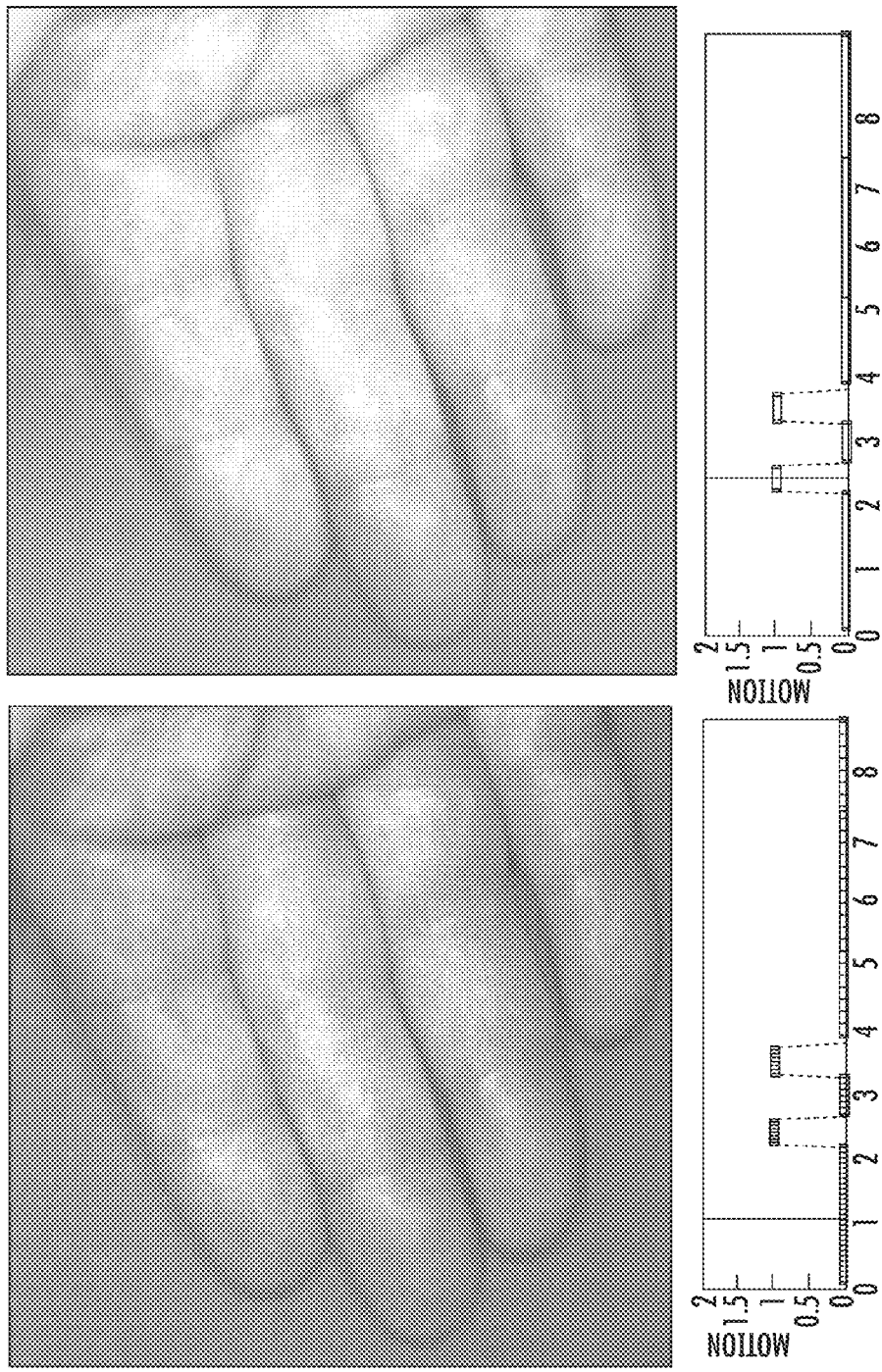

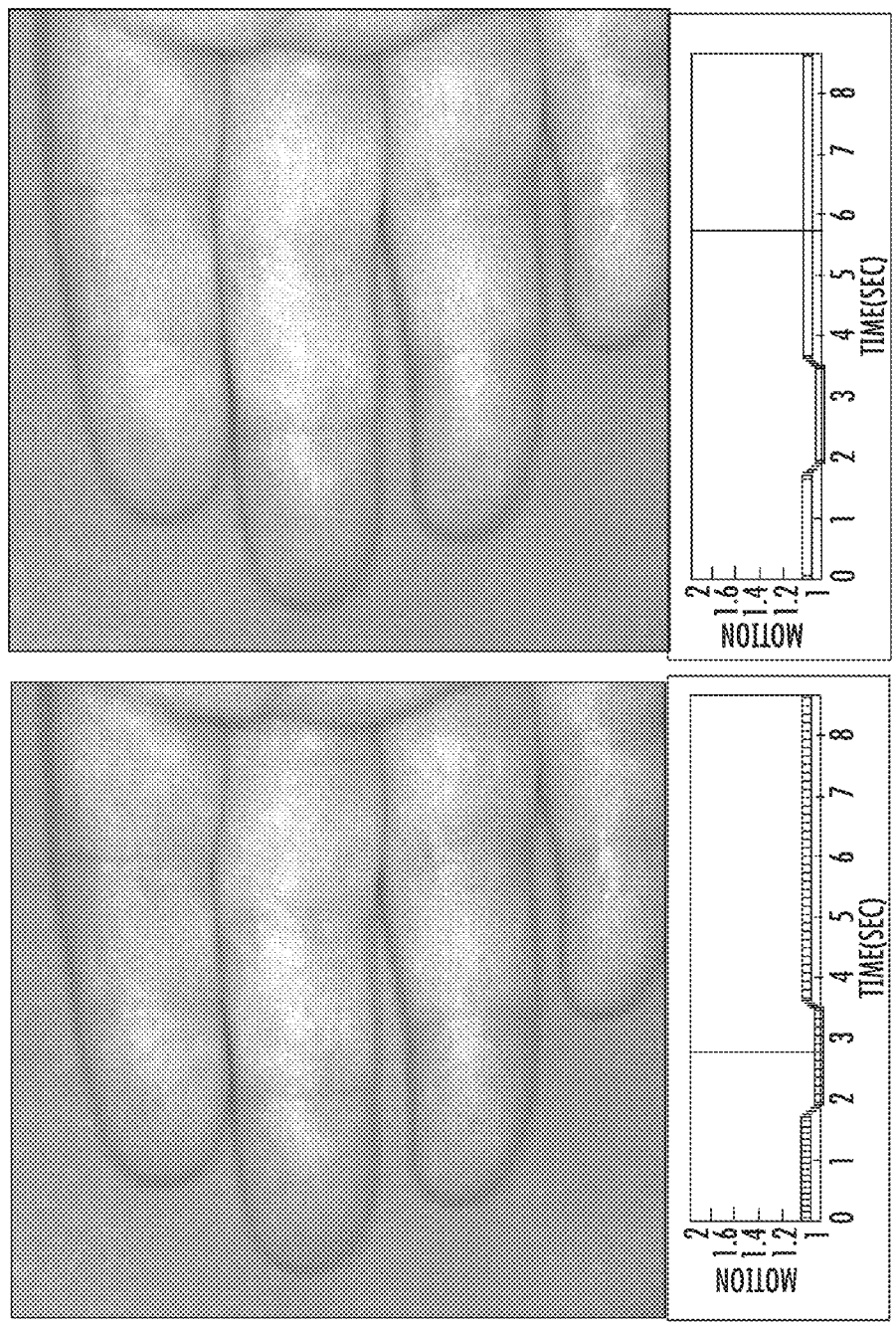

MULTI-SPECTRAL LASER IMAGING (MSLI) METHODS AND SYSTEMS FOR BLOOD FLOW AND PERFUSION IMAGING AND QUANTIFICATION

CLAIM OF PRIORITY

The present application claims the benefit of and priority to U.S. Provisional Application No. 62/136,010, filed Mar. 20, 2015, entitled Multi-Spectral Laser Imaging (MSLI) Methods and Systems for Blood Flow and Perfusion Imaging and Quantification, the disclosure of which is hereby incorporated herein by reference as if set forth in its entirety.

RESERVATION OF COPYRIGHT

A portion of the disclosure of this patent document contains material which is subject to copyright protection. The copyright owner, East Carolina University of Greenville, N.C., has no objection to the reproduction by anyone of the patent document or the patent disclosure, as it appears in the Patent and Trademark Office patent file or records, but otherwise reserves all copyright rights whatsoever.

FIELD

The present inventive concept relates generally to blood flow and perfusion quantification and, more particularly, to quantification of blood flow and perfusion in terms of distributions of blood velocity and blood flow rate in tissue/organs using imaging techniques, such as Laser Speckle Imaging, Laser Doppler Imaging and the like with multi-spectral capability.

BACKGROUND

The measurement results of blood flow and perfusion imaging technologies are typically disrupted by a motion artifact of the target tissue/organ in clinical circumstances. This movement can be micro (i.e., pulsatility of an arteriole due to systole and diastole blood pressure levels), intermediate (i.e., normal peristalsis of the small or large bowel) or macro (i.e., the movement of the heart during the cardiac cycle). This movement can be intrinsic to the imaged tissue (i.e., examples cited above), or extrinsic (i.e., the movement of the heart as a result of the movement of the lungs during ventilation). Thus, in many clinical situations, where accurate quantification of flow and perfusion is desirable, keeping the imaging target in a stationary status is difficult and, in some clinical scenarios, is not even possible. For example, such as imaging the distributions of blood flow velocity and flow rate for quantifying perfusion in coronary arteries and myocardium of a beating heart. Unfortunately, most conventional laser-based perfusion technologies either assume the target tissue/organ is stationary, which introduces significant inaccuracy or error in the clinical measurement of blood speed or velocity where the target is moving, such as a beating heart, or are simply provide no information for quantification of perfusion in terms of blood flow rate distribution that is critically needed in the clinical situation where the target may or may not be moving.

Tissues/organs in animals or human respond differently to light of different wavelengths. In general, light of shorter wavelengths can penetrate only the superficial layers of the tissues while light of longer wavelengths can penetrate both superficial layers and sub-surface layers in the spectral region from ultraviolet (UV) to near-infrared (NIR). UV and visible light of wavelengths less than, for example, 550 nm is optimal for detailed anatomic visualization in medicine when viewing the surface of tissues and organs. However, unlike NIR light, UV or visible light imaging is usually not inherently capable of revealing the physiological characteristics of tissues/organs in sub-surface layers, in part due to lack of penetration of the tissues/organs. Accordingly, improved methods of visualization and quantification are desired.

SUMMARY

Some embodiments of the present inventive concept provide multispectral imaging systems including a first light source having a first wavelength configured to image a sample; a second light source, different from the first light source, having a second wavelength, different from the first wavelength, configured to image the sample; a camera configured to receive information, for example, scattered light related to the first and second light sources from the sample, wherein the first wavelength is configured to reflect off a surface of the sample into the camera and the second wavelength is configured to penetrate the sample and provide information related to the sample to the camera; and a processor configured to combine the information related to the first and second light sources provided by the camera to image an anatomical structure of the sample, image physiology of blood flow and perfusion of the sample and/or synthesize the anatomical structure and the physiology of blood flow and perfusion of the sample in terms of blood flow rate distribution.

In further embodiments, the first and second wavelengths have different wavelengths in a range from 350 nm to 1100 nm.

In still further embodiments, the first wavelength may be in an ultraviolet (UV) or visible spectrum and the second wavelength may be in a visible or near-infrared spectrum.

In some embodiments, the sample may be at least one of tissue and an organ.

In further embodiments, the processor may be further configured to reconstruct a color image using one or more monochromatic cameras in real time.

In still further embodiments, the processor may be further configured to acquire scattered light in a visible or near-infrared (NIR) spectrum to provide deeper tissue information.

In some embodiments, an output of the system may provide a unique clarity of visualization.

In further embodiments, the processor may be further configured to quantitatively analyze the anatomical structure and physiology of blood flow and perfusion of the sample in terms of blood flow rate distribution.

In still further embodiments, the processor may be further configured to separate motion of the tissues/organs from motion of blood flow and perfusion in the imaged tissues/organs.

In some embodiments, the processor may be further configured to remove motion artifacts of the imaged sample, for example, tissues/organs, caused by physiologic and/or pathophysiologic movement of the imaged sample in order to improve accuracy of quantification of blood flow and perfusion.

In further embodiments, the processor may be further configured to remove motion artifact of the images sample caused by movement of an imaging platform/camera in order to improve accuracy of quantification of blood flow and perfusion.

In still further embodiments, the processor may be further configured to improve quantification accuracy in laser-based blood flow and perfusion measuring technologies by removing motion artifacts.

In some embodiments, the perfusion measuring technologies may include laser speckle imaging (LSI), laser Doppler imaging (LDI), Florescence imaging, reflectance imaging and/or LSI plus Fluorescence.

In further embodiments, the processor may be further configured to improve quantification accuracy in laser-based blood flow and perfusion measuring technologies by removing static background caused by a difference of the optical characteristics of an inhomogeneous scattering media.

In still further embodiments, the processor may be further configured to display anatomical structure and the physiology of blood flow and perfusion of an imaged sample, for example, an imaged tissue/organ simultaneously in real time.

In some embodiments, the processor may be further configured to image the anatomical structure and blood flow physiology at different depths in the sample.

In further embodiments, the first wavelength may be configured to extend from between 350 nm to 550 nm to between 300 nm to 600 nm into the sample and the second wavelength may be configured to penetrate the sample between 550 nm to 1100 nm to between 500 nm to 1500 nm.

Still further embodiments provide related methods and computer program products.

BRIEF DESCRIPTION OF THE DRAWINGS

FIGS. 7A and 7B are images illustrating the perfusion measurement using only near infra-red light (7A) and dual wavelength illumination 7B) of a shaking hand.

FIGS. 8A and 8B are images illustrating the perfusion measurement using only near infra-red light (8A) and dual wavelength illumination (8B) of a stationary hand with blood supply temporarily occluded by squeezing the wrist of the imaged hand using the other hand.

FIGS. 10A-10D are images illustrating a visible light image of a piece of small bowel of a pig as to define anatomical structure (10A); a near infra-red light image of the same piece of small bowel as to define the transparency map (10B); blood flow speed distribution map of the same piece of small bowel calculated by 11 frames of the NIR raw images using LSI (10C); and a combined visual effect using A, B, C using an algorithm in accordance with some embodiments of the present inventive concept to reveal both anatomical structure and blood flow physiology (10D).

FIGS. 11A-11C are images illustrating a visible light image of a piece of small bowel of a pig as to define anatomical structure by the brightness of the 8 bit grayscale image (11A); blood flow speed distribution map of the same piece of small bowel calculated by 11 frames of the NIR raw images using LSI (11B); and a combined visual effect using A and B using an algorithm in accordance with some embodiments of the present inventive concept to reveal both anatomical structure and blood flow physiology (11C).

FIGS. 12A-12D are images illustrating Panel A, an NIR 785 nm image of a small bowel (12A); Panel B a Green 532 nm image of the same small bowel (12B); Panel C, a reconstructed image of the same small bowel (12C); and Panel D, an image of the same small bowel taken by a regular camera (12D).

FIGS. 13A-13D are images illustrating Panel A, an NIR 785 nm image of a pig heart (13A); Panel B, Green 532 nm image of the same pig heart (13B); Panel C, a reconstructed image of the same pig heart (13C); and Panel D, an image of the same pig heart taken by a regular camera (13D).

FIGS. 14A-14E illustrate an image using a visible wavelength (532 nm) (14A); an image using near infra-red wavelength (785 nm) (14B); a reconstructed image (in gray scale) with the visible and infrared wavelengths (14C); a regular image with room light illumination (14D); and an image showing blood flow and perfusion image (14E).

FIGS. 15A-19B illustrate images that compensate for issues during clinical imaging procedures in accordance with some embodiments of the present inventive concept.

DETAILED DESCRIPTION

Figure 1:
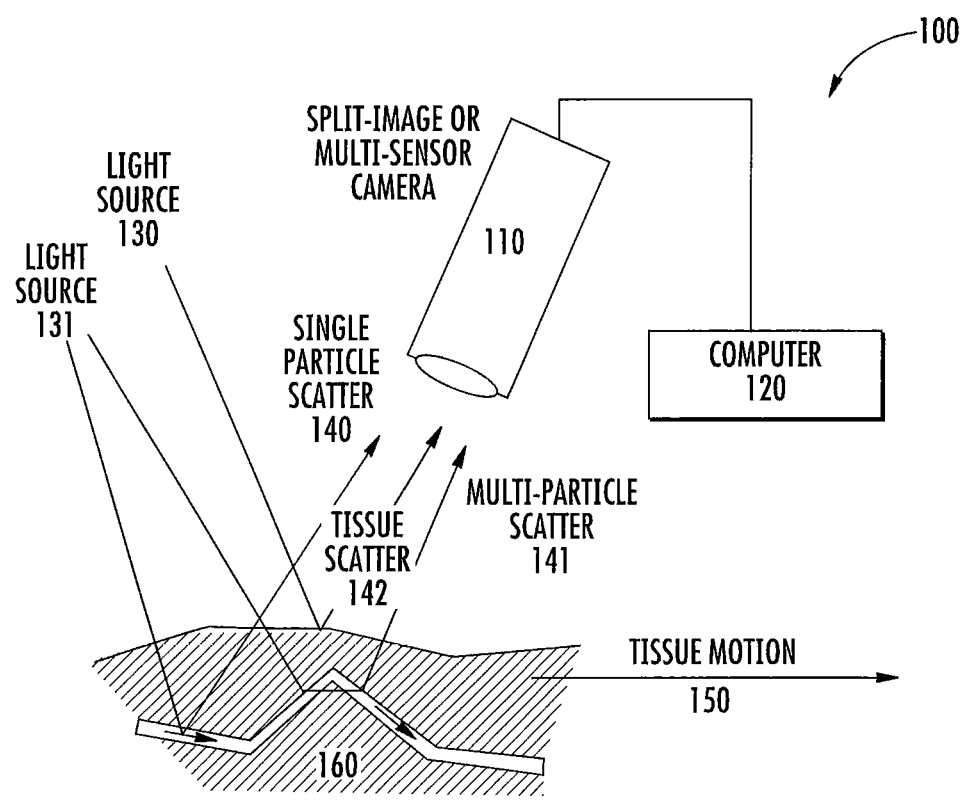
FIG. 1 is a block diagram illustrating a system implementing dual wavelength imaging in accordance with some embodiments of the present inventive concept.

Embodiments of the present inventive concept will now be described more fully hereinafter with reference to the accompanying figures, in which preferred embodiments of the inventive concept are shown. This inventive concept may, however, be embodied in many different forms and should not be construed as limited to the embodiments set forth herein. Like numbers refer to like elements throughout. In the figures, layers, regions, elements or components may be exaggerated for clarity. Broken lines illustrate optional features or operations unless specified otherwise.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the inventive concept. The sequence of operations (or steps) is not limited to the order presented in the claims or figures unless specifically indicated otherwise.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

As will be appreciated by one of skill in the art, embodiments of the present inventive concept may be embodied as a method, system, data processing system, or computer program product. Accordingly, the present inventive concept may take the form of an embodiment combining software and hardware aspects, all generally referred to herein as a "circuit" or "module." Furthermore, the present inventive concept may take the form of a computer program product on a non-transitory computer usable storage medium having computer usable program code embodied in the medium. Any suitable computer readable medium may be utilized including hard disks, CD ROMs, optical storage devices, or other electronic storage devices.

Computer program code for carrying out operations of the present inventive concept may be written in an object oriented programming language such as Matlab, Mathematica, Java, Smalltalk, C or C++. However, the computer program code for carrying out operations of the present inventive concept may also be written in conventional procedural programming languages, such as the "C" programming language or in a visually oriented programming environment, such as Visual Basic.

It will be understood that some embodiments of the present inventive concept implemented in Matlab may provide improved processing speeds in accordance with some embodiments of the present inventive concept.

Certain of the program code may execute entirely on one or more of a user's computer, partly on the user's computer, as a standalone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The inventive concept is described in part below with reference to flowchart illustrations and/or block diagrams of methods, devices, systems, computer program products and data and/or system architecture structures according to embodiments of the inventive concept. It will be understood that each block of the illustrations, and/or combinations of blocks, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer readable memory or storage that can direct a computer or other programmable data processing apparatus to function in a particular manner, such that the instructions stored in the computer-readable memory or storage produce an article of manufacture including instruction means which implement the function/act specified in the block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

The present inventive concept relates generally to blood flow and perfusion quantification and, more particularly, to quantification of blood flow and perfusion in tissue/organs in terms of distributions of blood velocity and blood flow rate using imaging techniques, such as Laser Speckle Imaging (LSI), Laser Doppler Imaging (LDI), Florescence imaging, reflectance imaging and the like with multispectral capability. Some embodiments of the inventive concept use two or more wavelengths in the range from 350 nm to 1100 nm to measure/quantify the blood velocity and blood flow rate distributions for quantification of perfusion, remove motion artifact and enhance visualization for presentation and real-time evaluation and assessment of the synthesized anatomical-physiological result. As used here, "Multispectral Laser Imaging (MSLI)" refers to imaging techniques using two or more wavelengths in accordance with some embodiments of the present inventive concept.

In particular, some embodiments of the present inventive concept provide a system that uses two wavelengths of differential transmittance through a sample to apply laser speckle or laser Doppler imaging. A first of the two wavelengths may be relatively small within the UV or visible range that has, such as blue light 450-495 nm. Light at this wavelength has very shallow penetration and images the anatomical structure of tissue/organ surface and serves as a position marker of the sample but not the subsurface movement of blood flow and perfusion. A second wavelength may be relatively large in the visible or near Infra-Red (NIR) range. Light at this wavelength has much larger penetration depth and reveals the underlying blood flow physiology and correlates both to the motion of the sample and also the movement of blood flow and perfusion. Using the imaging measurement of the visible light as a baseline, the true motion of blood flow and perfusion can be derived from the NIR imaging measurement without being affected by the motion artifact of the target. Furthermore, the anatomical structure information captured by visible light and the physiological characteristics measured by NIR light is combined as will be discussed herein.

As discussed in the background of the present application, using only visible or NIR spectrums may result in various issues with the final images produced. Accordingly, some embodiments of the present inventive concept combine different wavelengths of visible and NIR spectrum (350 nm-1100 nm) into an imaging system, such as LSI, LDI, Fluorescence, Reflectance or LSI plus Fluorescence and the like. The combination, as discussed herein, may reveal much more information of the tissue/organ than using one single wavelength. In particular, MSLI in accordance with some embodiments discussed herein can (1) account for and remove the motion artifact present in imaging clinical biologic structures, which creates blood flow and perfusion quantification inaccuracies; (2) improve visualization over current technologies by exact synthesis of both anatomic structure and the physiology of blood flow and perfusion simultaneously in real time; (3) through a combination of (1) and (2), improve the accuracy of quantification of blood flow and perfusion in clinical applications as will be discussed herein with respect to FIGS. 1 through 19B.

In some embodiments, in addition to using multiple wavelengths over the visible and NIR spectrum (350-1100 nm), embodiments of the present inventive concept can, for example, combine two or more laser imaging techniques such as near infra-red fluorescence (NIRF) and Laser Speckle Imaging (LSI), or NIRF and Laser Doppler Imaging (LDI), into one system as will also be discussed below with respect to the Figures.

Referring first to FIG. 1, a block diagram illustrating a simplistic system implementing dual wavelength imaging in accordance with some embodiments of the present inventive concept will be discussed. As illustrated in FIG. 1, the system 100 includes at least two light sources, first 130 and second 131 light sources, respectively, a sample 160, a camera 110 and a communications device (computer 120). In some embodiments of the present inventive concept, the first light source delivers visible light 130 and the second light source delivers NIR 131 light. As discussed above, the coherent short wavelength 130 (visible source) does not penetrate deep into the sample 160 (tissue/organ), but provides detail of the surface of the sample 160 in the tissue scatter (142). In contrast, the coherent NIR source 131 penetrates deep into the sample 160 and may provide single (140) or multi particle (141) scatter. The reflections 140, 141, 142 off the sample 160 are captured by a camera 110, which may be, for example, a split-image or multi-sensor camera. In particular, in some embodiments the camera may be a multi-sensor camera, rather than a single camera with one sensor chip. The multi-sensor camera has multiple sensors and each sensor is configured to image one wavelength or wavelength range.

The information can be processed by the communications device 120, which combines the visible and NIR wavelength images to provide improved blood flow and perfusion data in accordance with some embodiments of the present inventive concept. As will be understood, the data provided by embodiments discussed herein account for movement 150 of the sample (tissue/organ) 160 and provide a much improved image thereof.

Figure 2:
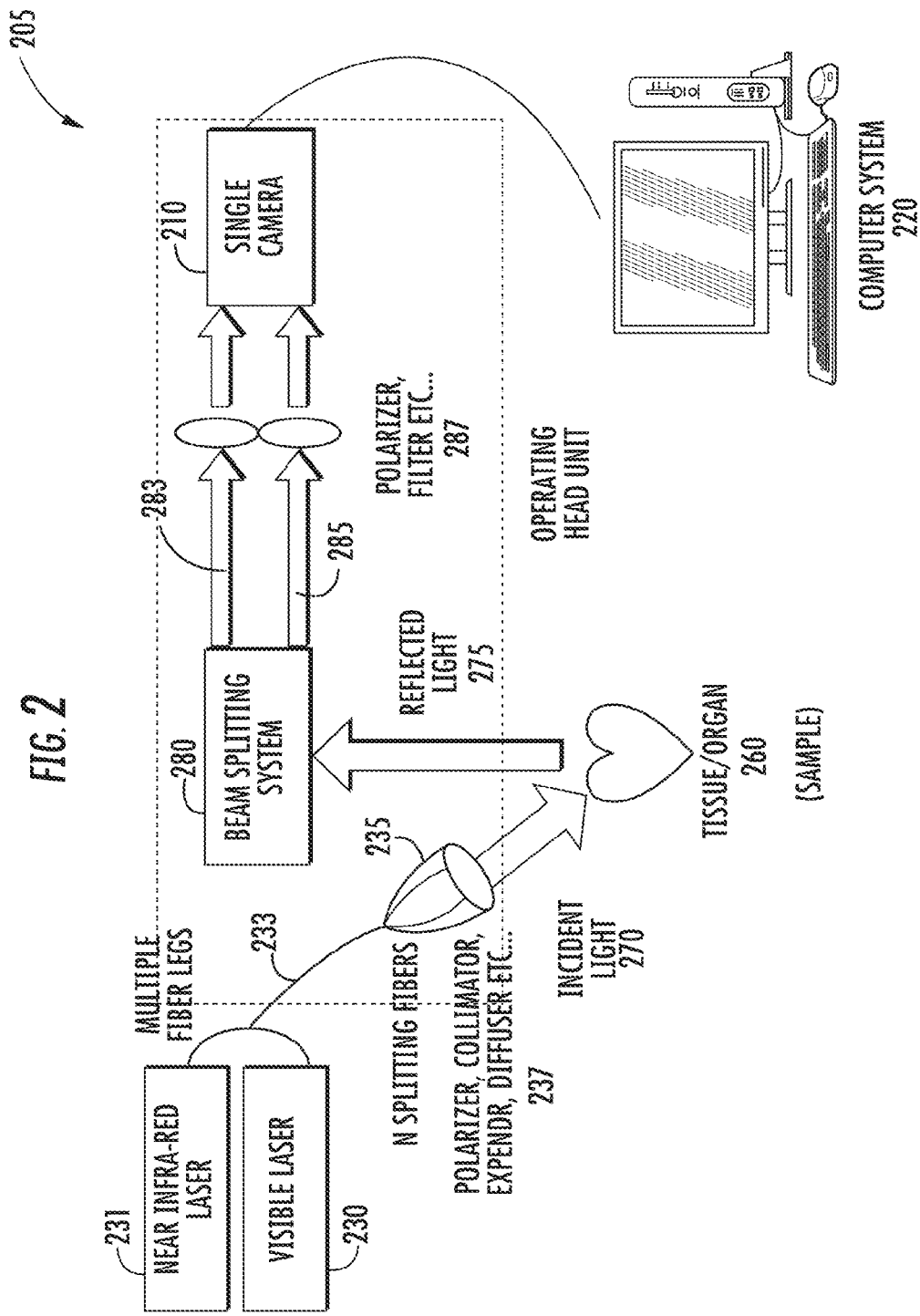
FIG. 2 is a more detailed block diagram illustrating various components of a multi-wavelength imaging system in accordance with some embodiments of the present inventive concept.

Referring now to FIG. 2, a more detailed block diagram illustrating various components of a multi-wavelength imaging system in accordance with some embodiments of the present inventive concept will be discussed. As illustrated in FIG. 2, the system 205 includes at least two laser light sources, visible 230 and NIR 231, a connecting fiber 233, components of an imaging system 237, a sample 260, a beam splitter 280, a camera 210 and a communications device (computer system 220). In operation, when the NIR laser 231 delivers NIR light to a living sample 260, such as a tissue/organ, a portion of the NIR light will go through single or multiple scattering of both stationary and moving particles inside the sample and reflect back. When the visible laser 230 delivers non-penetrating visible light, such as light having 43 nm, to a living sample 260, such as a tissue/organ, most of the light will be reflected back by the surface within less than 100 µm depth. For the NIR laser 231, approximately ninety five percent of the light will be returned from a top 700 µm of the sample 260, which is enough penetration to pass through coronary artery walls at, for example, a 300 µm depth, and generate information from moving particles, such as red blood cells, as well as from stationary tissue.

The reflected visible light contains the surface movement information of the sample 260 and, thus, reflects the motion artifact. The reflected NIR light contains the surface and subsurface movement information of the sample 260 and, thus, reflects both motion artifact and movement of the blood flow. As illustrated in FIG. 2, the light produced by the lasers 230 and 231 may be provided to a fiber 233, which may have multiple fiber legs and may include a plurality of splitting fibers 235 as illustrated. However, embodiments of the present inventive concept are not limited to the configuration illustrated in FIG. 2. For example, more or less fibers may be used without departing from a scope of the present inventive concept. Furthermore, the light on the fibers may pass through various elements of an imaging system 237 before reaching the sample 260. For example, the light may traverse polarizers, collimators, expanders, diffusers and the like before reaching the sample 260 without departing from the scope of the present inventive concept.

The incident light 270 illuminates the sample 260 and the reflected light 275 is provided to a beamsplitter 280. In some embodiments of the present inventive concept, the beamsplitter 280 may be a dichroic beam splitting system that separates the NIR 283 and visible light 285. The separated light 283 and 285 may pass through polarizers, filters and the like 287 before being delivered to the camera 210. As discussed above, the camera 210 can be, for example, a split-image or multi-sensor camera without departing from the scope of the present inventive concept. As stated, the multi-sensor camera has multiple sensors each configured to image a wavelength or wavelength range.

The NIR 283 and visible 285 images are redirected to the camera 210 and a split image is created on one camera sensor or on separate camera sensors that have been synchronized and aligned. As discussed above, different wavelengths have different penetration levels in the tissue/organ. Using multi-spectrum image design as discussed herein, the anatomical structure and blood flow physiology at different depths in the tissue/organ can be revealed as will be discussed below with respect to various figures.

Figure 3:
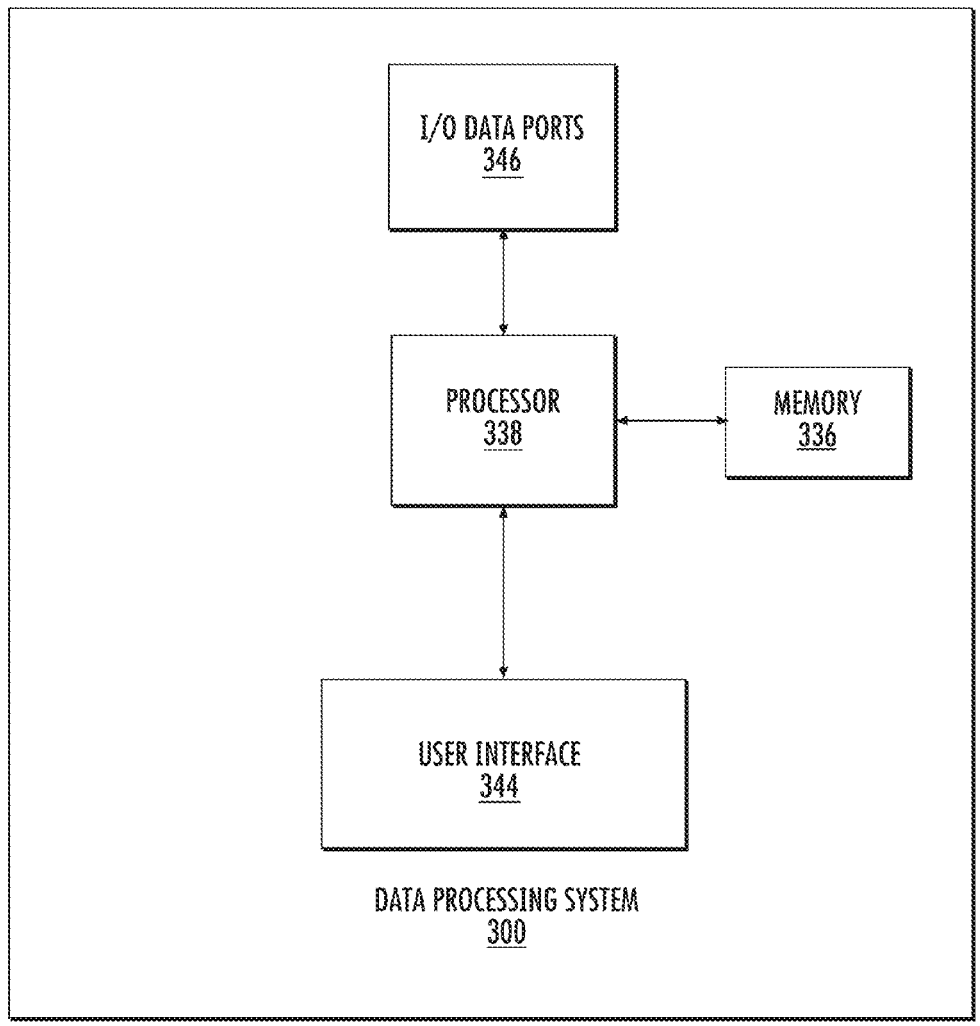
FIG. 3 is a block diagram of a data processing system according to some embodiments of the present inventive concept(s).

As illustrated in FIGS. 1 and 2, systems in accordance with embodiments of the present inventive concept include communications devices 120, 220, which are used for the various processing necessary to implement embodiments of the present inventive concept. Referring now to FIG. 3, a data processing system 300 that may be used in the systems of FIGS. 1 and 2, for example, in the communications devices 120, 220, in accordance with some embodiments of the inventive concept will be discussed. It will be understood that the data processing system 300 may be included in any of the components of the system without departing from the scope of the present inventive concept. For example, the data processing system 300 may be included in the camera 110, 210 or split between various elements of the system without departing from the scope of the present inventive concept.

Referring now to FIG. 3, an exemplary embodiment of a data processing system 300 suitable for use in the systems of FIGS. 1 and 2 includes a user interface 344 such as a keyboard, keypad, touchpad or the like, I/O data ports 346 and a memory 336 that communicates with a processor 338. The I/O data ports 346 can be used to transfer information between the data processing system 300 and another computer system or a network. These components may be conventional components, such as those used in many conventional data processing systems, which may be configured to operate as described herein.

Figure 4:
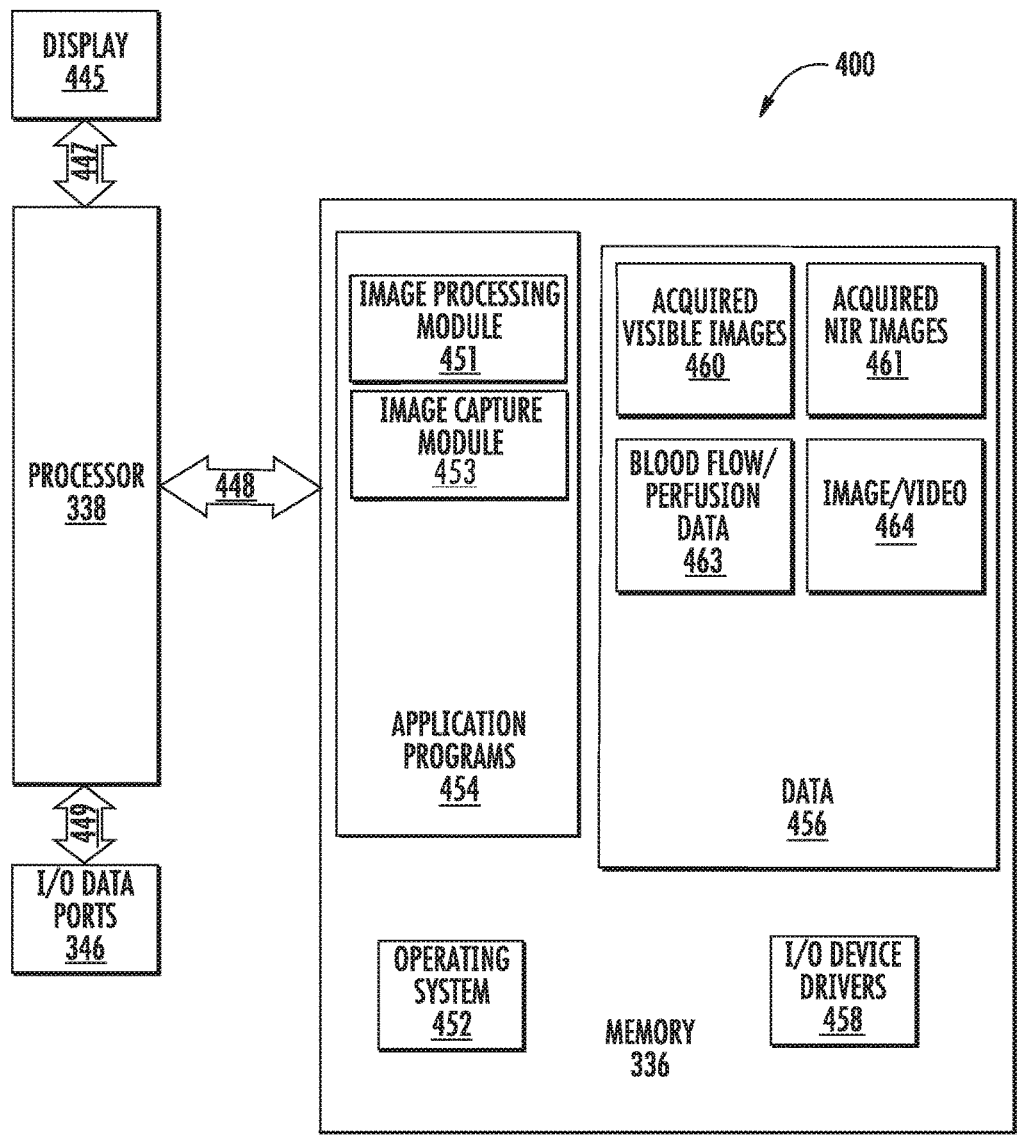
FIG. 4 is a more detailed block diagram of the data processing system illustrated in FIG. 3 in accordance with some embodiments of the present inventive concept(s).

Referring now to FIG. 4, a more detailed block diagram of the data processing system 400 in accordance with some embodiments of the present inventive concept will be discussed. The processor 338 communicates with a display 445 via and address/data bus 447, the memory 336 via an address/data bus 448 and the I/O data ports 346 via an address/date bus 449. The processor 338 can be any commercially available or custom microprocessor or ASICs. The memory 336 is representative of the overall hierarchy of memory devices containing the software and data used to implement the functionality of the data processing system 400. The memory 336 can include, but is not limited to, the following types of devices: cache, ROM, PROM, EPROM, EEPROM, flash memory, SRAM, and DRAM.

As illustrated in FIG. 4, the memory 336 may include several categories of software and data used in the data processing system 400: an operating system 452; application programs 454; input/output (I/O) device drivers 458; and data 456. As will be appreciated by those of skill in the art, the operating system 452 may be any operating system suitable for use with a data processing system, such as OS/2, AIX or zOS from International Business Machines Corporation, Armonk, N.Y., Windows95, Windows98, Windows2000, WindowsXP, or Vista from Microsoft Corporation, Redmond, Wash., Unix, Linux, LabView, or a real-time operating system such as QNX or VxWorks, or the like. The I/O device drivers 458 typically include software routines accessed through the operating system 452 by the application programs 454 to communicate with devices such as the I/O data port(s) 346 and certain memory 336 components. The application programs 454 are illustrative of the programs that implement the various features of the data processing system 400 included in a system in accordance with some embodiments of the present inventive concept and preferably include at least one application that supports operations according to some embodiments of the present inventive concept. Finally, the data 456 represents the static and dynamic data used by the application programs 454, the operating system 452, the I/O device drivers 458, and other software programs that may reside in the memory 336.

As illustrated in FIG. 4, the data 456 according to some embodiments of the present inventive concept may include acquired visible images 460, acquired NIR images/data 461, calculated blood flow/perfusion data 463 and images/video 464. Although the data 456 illustrated in FIG. 4 includes four different files 460, 461, 463 and 464, embodiments of the present inventive concept are not limited to this configuration. Two or more files may be combined to make a single file; a single file may be split into two or more files and the like without departing from the scope of the present inventive concept.

As further illustrated in FIG. 4, the application programs 454 may include an image processing module 451 and an image capture module 453 in accordance with some embodiments of the inventive concept. While the present inventive concept is illustrated, for example, with reference to the image processing module 451 and the image capture module 453 being application programs in FIG. 4, as will be appreciated by those of skill in the art, other configurations may also be utilized while still benefiting from the teachings of the present inventive concept. For example, the image processing module 451 and the image capture module 453 may also be incorporated into the operating system 452 or other such logical division of the data processing system 400. Thus, the present inventive concept should not be construed as limited to the configuration of FIG. 4, but is intended to encompass any configuration capable of carrying out the operations described herein.

Furthermore, while the image processing module 451 and the image capture module 453 are illustrated in a single data processing system, as will be appreciated by those of skill in the art, such functionality may be distributed across one or more data processing systems. Thus, the present inventive concept should not be construed as limited to the configurations illustrated in FIGS. 3 and 4, but may be provided by other arrangements and/or divisions of function between data processing systems.

In certain embodiments, such as an LSI application, the velocity of a target fluid can be calculated using the following equation:

$$v(i, j) = v_0 + \frac{a}{C(i, j)^2} \qquad \text{Eqn. (1)}$$

where $v(i,j)$ is the velocity of target fluid, $v_0$ is an added term to account for background noise and may be zero after the baseline has been removed; a is a constant related to imaging parameters, laser parameters, time/spatial smoothing parameters for obtaining c and reflects the optical characteristics of the target fluid; c is the laser speckle contrast; and i and j are the row and column pixel index.

For an LDI application, the velocity of a target fluid can be calculated using the following equation:

$$v(i, j) = \frac{\lambda}{2\sin\theta}\Delta f \qquad \text{Eqn. (2)}$$

where $v(i,j)$ is velocity of target fluid; where $\lambda$ is the wavelength; $\Delta f$ is the change in Doppler frequency (Doppler frequency shift); and $\theta$ is half of the angle between the two beams. Typically, there is no direct formula to apply for NIRF, and the like.

However, even when the imaged object is stationary, there is movement present that must be accounted for to accurately determine blood flow in vessels and perfusion in tissue. As recently as 2013, experts in the field of LSI discussed motion artifact as one of the two key questions still to be answered in this field. Therefore, systems and methods that have the capability to identify this motion contribution and account for its magnitude are needed and included in technologies claiming to be able to assess, image, and/or quantify blood flow in vessels and perfusion in tissues experimentally and in vivo.

Figure 5A:
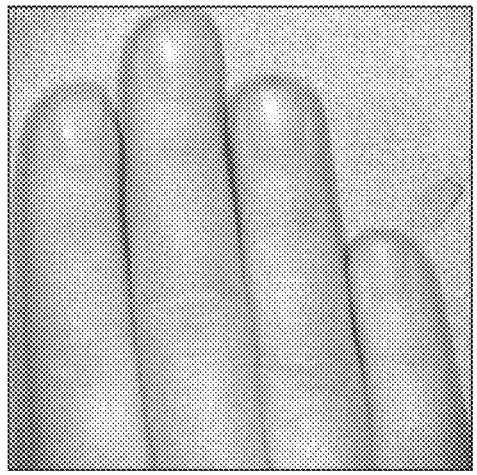
FIGS. 5A and 5B are a visible light image (5A) and a near infra-red light image (5B) of a hand.
Figure 5B:
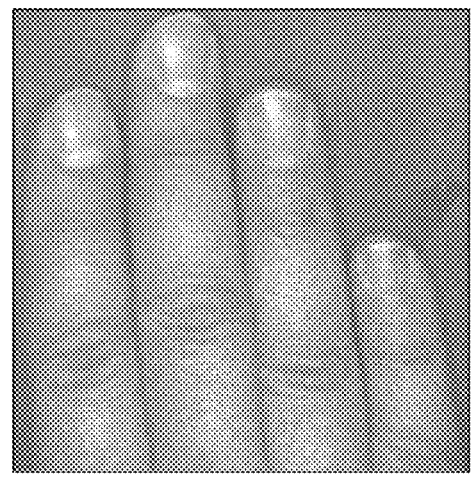

Referring now to FIGS. 5A and 5B, FIG. 5A is a visible light image of a hand and FIG. 5B is a near infra-red light image of a hand. These images may be used to calculate the motion artifact and the movement of the blood flow and perfusion in accordance with some embodiments of the present inventive concept.

In particular, to remove the motion artifact of the tissue/organ that is caused by movement of tissue/organ, such as aspiration, spasm, heart beat and the like and/or the camera, Galilean velocity addition can be calculated using the following equation:

$$v_{12}(r) = v_{13}(r) + v_{32}(r) = v_{13}(r) - v_{23}(r) \qquad \text{Eqn. (3)}$$

where: $v_{13}(r)$ is the velocity distribution of object of interest (blood flow and perfusion) relative to detector (camera); $v_{23}(r)$ is the velocity distribution of the host object (the tissue/organ in which the blood vessel is embedded) relative to detector (camera); and $v_{12}(r)$ is the velocity distribution of an object of interest (blood flow and perfusion) relative to the host object (the tissue/organ in which the blood vessel is embedded). Thus, embodiments of the present inventive concept may address a need to determine $v_{12}(r)$ under the condition that the image signals by the all the current LSI or LDI method provides only $v_{13}(r)$. According to some embodiments of the present inventive concept, the multi spectrum imaging approach, both $v_{13}(r)$ and $v_{23}(r)$ can be made available.

Using LSI as an example, using the Eqn. (1) above, the speckle contrast of coherent NIR laser light $C_{NIR}(i,j)$ is associated with $v_{13}(r)$, which is the velocity distribution of an object of interest (blood flow and perfusion) relative to detector (camera). $v_{13}(r)$ is affected by the movement of blood flow and the movement of tissue/organ caused by factors such as aspiration, spasm, heart beat etc. and the movement of the camera. The visible laser light, especially within the 450-495 nm wavelength range (blue laser light), has much less penetration in soft tissue/organ compared with the NIR laser light.

Using Eqn. (1) set out above, the speckle contrast of coherent visible laser light $C_{VIS}(i,j)$ is mainly associated with $v_{23}(r)$, which is the velocity distribution of the host object (the tissue/organ that the blood vessel is embed) relative to detector (camera). $v_{23}(r)$ is affected by the movement of tissue/organ caused by factors such as aspiration, spasm, heart beat etc. and the movement of the camera. Using Eqn. (3), $v_{12}(r)$ can be derived using $v_{13}(r)$ and $v_{23}(r)$ thus the velocity distribution of object of interest (blood flow and perfusion) relative to the host object (the tissue/organ that the blood vessel is embed) can be quantified without the effect of the movement of tissue/organ and the movement of the camera.

The speckle contrast of coherent visible laser light $C_{VIS}(i,j)$ as a baseline can be used to normalize the speckle contrast of coherent NIR laser light $C_{NIR}(i,j)$ based on this mathematic model to reduce the velocity component of the motion artifact. Computer algorithms may be designed to normalize (subtract or divide) $C_{NIR}(i,j)$ using $C_{VIS}(i,j)$ to yield one or multiple stabilized blood flow and perfusion maps in real time. The algorithms may be processed by, for example, a data processor as discussed above with respect to FIGS. 3-4.

Figure 6A:
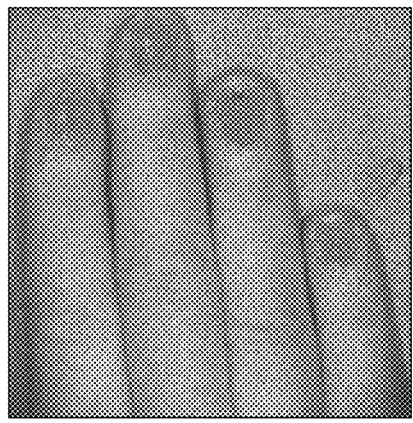
FIGS. 6A and 6B are images illustrating the perfusion measurement using only near infra-red light (6A) and dual wavelength illumination (6B) of a stationary hand.
Figure 6B:
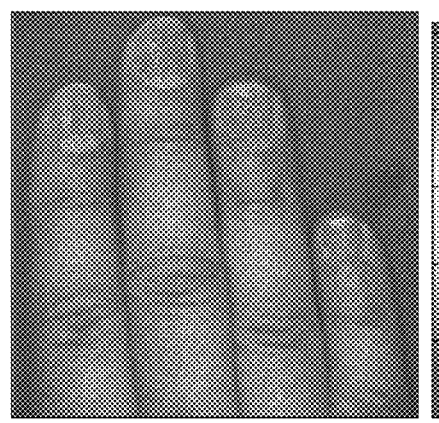

Referring now to FIGS. 6A and 6B, images generated using the measurement of the blood flow and perfusion using only NIR and dual wavelength illumination of a stationary hand will be discussed. As illustrated, the measurement of the blood flow and perfusion using only NIR and dual wavelength illumination of a stationary hand are very similar. This is because when the sample/target is stationary, the motion artifact as baseline measured by visible light is close to zero. Thus, the result without removing the baseline (FIG. 6A: using only NIR light) and the result with the baseline removed (FIG. 6B: using dual wavelength illumination) are almost identical.

Referring now to FIGS. 7A and 7B, images illustrating the measurement of the blood flow and perfusion using only NIR and dual wavelength illumination of a shaking hand will be discussed. As illustrated therein, the measurement of the blood flow and perfusion using only NIR and dual wavelength illumination of a shaking hand are very different. The measurement with only NIR light (FIG. 7A) shows much higher perfusion level which is caused by the motion artifact. The measurement with dual wavelength illumination (FIG. 7B) is almost identical to the measurement of the stationary hand. This is because when the sample/target is moving the motion artifact as baseline measured by visible light is not zero. Thus, the result without removing the baseline (FIG. 7A: using only NIR light) shows more "blood flow and perfusion" than the result with the baseline removed (FIG. 7B: using dual wavelength illumination).

Referring now to FIGS. 8A and 8B, images illustrating both the perfusion measurement with only NIR and the dual wavelength illumination will be discussed. In particular, FIGS. 8A and 8B are images illustrating the perfusion measurement using only near infra-red light (8A) and dual wavelength illumination (8B) of a stationary hand with blood supply temporarily occluded by squeezing the wrist of the imaged hand using the other hand. As illustrated, a decrease induced by the temporary occlusion of the blood supply to the hand is clear.

Different from LSI, LDI uses interference of two coherent light beams: the one from the laser as the light source and the one reflected from the moving object whose frequency is slightly shifted from that of the incident light. LDI determines the speed of one "pixel" or points or a small region of the object where the incident beam is focused on. An image is obtained by scanning the focused beam. Similar to the LSI of Eqn. (1) using Eqn. (2), measurement of $v_{13}(r)$ and $v_{23}(r)$ in LDI can be achieved using a penetrating NIR beam and a non-penetrating visible beam. Again, using Eqn. (3) $v_{12}(r)$ of the fiducial points relative to the host object (the tissue/organ that the blood vessel is embed) can be identified.

Figure 9A:
FIGS. 9A and 9B illustrated perfusion measurement using only near infra-red light (9A) and dual wavelength illumination (9B) of a large bowel of a pig.
Figure 9B:
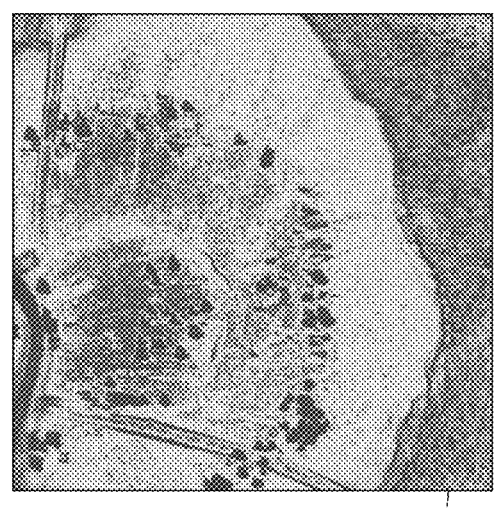

Furthermore, practically, the laser speckle contrast is a mixture of static background and dynamic part. The dynamic part of the speckle contrast is associated with the motion and the static background is caused by the difference of the optical characteristics of the inhomogeneous scattering media. Since among the current LSI technologies, baseline speckle contrast at a no flow situation is not available, other than in a controlled phantom/tubing experiment, the static background of the speckle contrast is a major obstacle to accurately quantifying blood flow in tissue/organ. Multi-spectrum illumination schemes provide a baseline speckle contrast at no flow situation $C_{VIS}(i,j)$ using visible coherent laser light. The speckle contrast of coherent visible laser light $C_{VIS}(i,j)$ can be used to normalize the speckle contrast of coherent NIR laser light $C_{NIR}(i,j)$ based a mathematic model in accordance with embodiments of the present inventive concept to reduce the static background in the speckle contrast as illustrated in FIGS. 9A and 9B. FIGS. 9A and 9B illustrate perfusion measurement using only near infra-red light (9A) and dual wavelength illumination (9B) of a large bowel of a pig. Measurement inaccuracy caused by the static contrast can be seen on the surgical drape 950 in FIG. 9A. In FIG. 9B, the "fake" blood flow and perfusion is not visible on the surgical drape 950 due to reduction of the static contrast.

Embodiments of the present inventive concept propose the visualization of both anatomical structure and blood flow physiology of the tissue and organ by one of two approaches. However, it will be understood that embodiments of the present inventive concept are not limited to the approaches discussed herein.

Referring now to FIG. 10A-10D, a first approach using a dual layer design will be discussed. Referring first to FIG. 10A (Panel A), an anatomical layer represented by a raw (original) image frame of visible light is illustrated. (Anatomical layer) $Img_{VIS}(i,j)$ is an 8 bit gray scale visible image of the sample/target tissue/organ and i and j are the pixel indexes along the horizontal and vertical direction. In some embodiments, the brightness, contrast and gamma value of this image might be adjusted to achieve better visualization effect.

Referring now to FIG. 10B, a processed image is produced based on one or more raw image frames of near infra-red light to reflect two-dimensional (2D) speed distribution' of blood flow and perfusion of the imaged tissue/organ using Laser Speckle or Laser Doppler Imaging technology. (Physiological layer) $Img_{NIR}(i,j)$ is an 8 bit indexed image with its numerical values mapped to a predefined color map. Usually, the color ranges from blue to red (0 to 255) with blue representing no/minimum flow speed and red representing the highest flow speed that the system can detect.

Referring now to FIG. 10C, a transparency map is produced using methods that overlap the anatomical layer or parts of the anatomical layer over a physiological one, which will cause the bottom layer to be invisible (covered) or partially invisible (covered). Methods that overlap the physiological layer or parts of the physiological layer over anatomical one will cause the bottom layer to be invisible (covered) or partially invisible (covered). A transparency map/matrix is applied in accordance with embodiments of the present inventive concept to ensure the visibility of both layers using the following equation:

$$T(i,j) = \left( \frac{Img(i,j) - \text{Min}(Img(i,j))}{\text{Max}(Img(i,j)) - \text{Min}(Img(i,j))} \right)^x \quad \text{Eqn. (4)}$$

where $T(i,j)$ is the transparency map with Img being a raw (original) image frame of visible or near infra-red light and x being an adjustable parameter >0 and <=2. Basically, each pixel value in $T(i,j)$ is between 0 and 1 with 0 representing no transparency and 1 representing 100% transparency. Parameter x controls the contrast of the transparency map and if x>1, transparency has a larger dynamic range and if x<1, the transparency has a smaller dynamic range. FIG. 10D represents the combined visual effect using A, B and C in accordance with embodiments of the present inventive concept to reveal both anatomical structure and physiology.

Referring now to FIGS. 11A through 11C, a second approach using color and brightness design will be discussed. As illustrated in FIG. 11A, an anatomical layer is represented by image brightness: a raw (original) image frame of visible light. $Img_{VIS}(i,j)$ is an 8 bit gray scale visible image of the sample/target tissue/organ and i and j are the pixel indexes along horizontal and vertical direction. The brightness, contrast and gamma value of this image may be adjusted to achieve better visualization effect.

Referring now to FIG. 11B, a physiological layer is represented by image color: a processed image based on one or more raw image frames of near infra-red light to reflect 2D speed distribution of blood flow velocity and perfusion of the imaged tissue/organ using Laser Speckle or Laser Doppler Imaging technology. In a first step, an 8 bit indexed color image is generated with its numerical values mapped to a predefined color map. Usually, the color ranges from blue to red (0 to 255) with blue representing no/minimum flow speed and red representing the highest flow speed that the system can detect. In a second step, the 8 bit indexed color image is converted to a normalized RGB map $RGB_{NIR}(i,j)$ with the color of each pixel being represented by (R, G, B) three values and each value range from 0~1. It will be understood that since the Figures are in black and white, the corresponding grey scale has been employed herein.

Referring now to FIG. 11C, anatomical and physiological layers are fused together by creating an 8 bit RGB color image as $Img(i,j)=Img_{VIS}(i,j) \times RGB_{NIR}(i,j)$. Note, each color channel (matrix $R_{NIR}(i,j)$, $G_{NIR}(i,j)$ and $B_{NIR}(i,j)$) is multiplied by the same visible image $Img_{VIS}(i,j)$.

According to some embodiments of the present inventive concept, multi wavelength imaging design may be used to simultaneously combine different imaging technologies together. For example, as discussed herein, NIR fluorescence technology based on indocyanine green uses 808 nm illumination and the fluorescence emission light is 830 nm and 808 nm reflection light is considered as noise and filtered out. In accordance with some embodiments of the present inventive concept, the 808 nm reflection light can be used to achieve LSI or LDI while maintaining the 830 nm fluorescence function.

Referring now to FIGS. 12A-12D, images illustrating Panel A, an NIR 785 nm image of a small bowel (12A); Panel B a Green 532 nm image of the same small bowel (12B); Panel C, a reconstructed color image of the same small bowel (12C); and Panel D, an image of the same small bowel taken by a regular camera (12D) will be discussed. In particular, using the multi spectral imaging system in accordance with some embodiments of the present inventive concept, an original color image can be constructed by using each spectrum as one RGB color channel. For example, using an NIR image as a red color channel and a 532 nm image as a green color channel, the color image of a small intestine can be generated without using a color camera as illustrated in FIGS. 12A-12D. It will be understood that since the Figures are black and white, the corresponding grey scale has been employed herein.

Referring now to FIGS. 13A-13D, images illustrating Panel A, an NIR 785 nm image of a pig heart (13A); Panel B, Green 532 nm image of the same pig heart (13B); Panel C, a reconstructed color image of the same pig heart (13C); and Panel D, an image of the same pig heart taken by a regular camera (13D) will be discussed. FIGS. 13A-13D illustrate using an NIR image as a red color channel and a 532 nm image as a green color channel, the color image of a pig heart can be generated without using a color camera. If the information of one color channel is missing, an algorithm is designed to generate this data using the information of the other two color channels. Since the color of a sample (tissue/organ) is mainly red, embodiments of the present inventive concept can generate color that is very close to the original one as long as the information of the red color channel is available as discussed with respect to FIGS. 10A-10D and 11A-11D. Thus, embodiments of the present inventive concept allow the reconstructed color image to reveal information of deeper tissue/organ if NIR is used as the red color channel as shown in Panel C (FIG. 12C) vs. Panel D (FIG. 12D).

As discussed briefly above with respect to the Figures, some embodiments of the present inventive concept use two wavelengths of differential transmittance through target tissue to apply LSI or LDI. In some embodiments, a first wavelength is within in the visible range having zero or very shallow penetration, such as blue light (450-495 nm). The imaging result of this non-penetrating illumination serves as capturing the anatomical structure of tissue/organ surface and position marker of the target tissue/organ, but not the subsurface movement of blood flow and perfusion. A second of the two wavelengths is Near Infra-Red (NIR), which has much deeper penetration and the imaging result of this NIR illumination reveals the underlying blood flow physiology, which correlates both to the motion of the target tissue/organ and also the movement of blood flow and perfusion.

Using the imaging measurement of the visible light as a baseline, the true motion of blood flow and perfusion can be derived from the NIR imaging measurement without being affected by the motion artifact of the target. Furthermore, the anatomical structure information captured by visible light and the physiological characteristics measured by NIR light may be synthesized together according to some embodiments of the present inventive concept. The synthesized imaging product according to embodiments discussed herein provides a previously unattainable clarity of visualization and accuracy of quantification of blood flow and perfusion across the spectrum of clinical applications of laser imaging technologies.

Thus, embodiments of the present inventive concept provide improved image quality and real time data acquisition (several seconds vs minutes for all other technologies) and analysis. This real time aspect of the present inventive concept makes this technology a real option for sustained adoption of the technology by a surgeon/provider. Embodiments of the present inventive concept accurately depict and quantify blood flow and perfusion.

Further embodiments of the present inventive concept are directed to color image reconstruction using multi-wavelength imaging techniques discussed herein. It will be understood that the images are present in a gray scale as the patent application publishes in black and white. In particular, using a dual wavelength imaging technique as discussed herein, two images may be acquired simultaneously. One is near infra-red image IR(x,y) and the other is a visible image VIS(x,y). X and Y represent the index of the horizontal and vertical pixel. To reconstruct a red green blue (RGB) color image, red, green and blue channels are calculated separately as follows:

$$R(x, y) = (2^N - 1) \times a_1 \times \left(\frac{NIR(x, y) - \min(NIR(x, y))}{\max(NIR(x, y)) - \min(NIR(x, y))}\right)^{b_1} \quad \text{Eqn. (5)}$$

$$G(x, y) = (2^N - 1) \times a_2 \times \left(\frac{VIS(x, y) - \min(VIS(x, y))}{\max(VIS(x, y)) - \min(VIS(x, y))}\right)^{b_2} \quad \text{Eqn. (6)}$$

$$B(x, y) = (2^N - 1) \times a_3 \times \left(\frac{VIS(x, y) - \min(VIS(x, y))}{\max(VIS(x, y)) - \min(VIS(x, y))}\right)^{b_3} \quad \text{Eqn. (7)}$$

$$\frac{NIR(x, y) - \min(NIR(x, y))}{\max(NIR(x, y)) - \min(NIR(x, y))} \quad \text{Eqn. (8)}$$

where R(x,y), G(x,y), B(x,y) are the red, green and blue channels, respectively, of the RGB color image; N is the bit of the color map, for example, 8 bit or 16 bit; a and b are the adjusting parameters for each channel; min is the function to get the minimum value; max is the function to get the maximum value; and Eqn. (8) serves as a normalization of the original image of one specific wavelength. Furthermore, the brightness, contrast and gamma value of the original image of one specific wavelength might be adjusted before applying the equations above.

The multi-wavelength color image recreation technique in accordance with some embodiments of the present inventive concept may reduce the need for an extra color camera in the device; can create a color image with a minimum of two wavelengths; and compared with traditional color images, the color image produced in accordance with embodiments discussed herein visualizes a larger depth of penetration due to use of near infra-red wavelength.

Figure 14A:
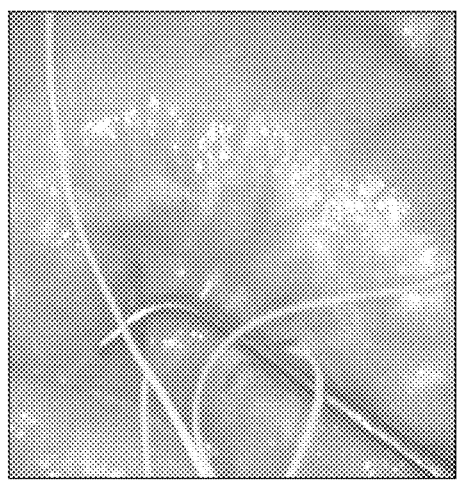
Figure 14B:
Figure 14C:
Figure 14D:
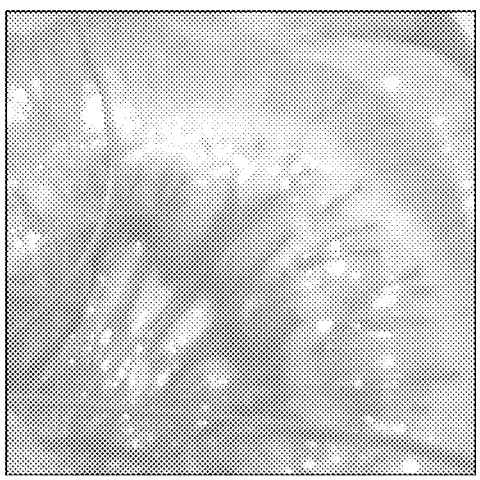

Referring now to FIGS. 14A through 14E, various images of a segment of a large bowel of a pig imaged using the multi-wavelength imaging device in accordance with some embodiments of the present inventive concept will be discussed. FIG. 14A is an image of the bowel of the pig obtained using a visible wavelength (532 nm). FIG. 14B is an image of the bowel of the pig using a near infra-red wavelength (785 nm). FIG. 14C is an image of the bowel of the pig reconstructed with the wavelengths of FIGS. 14A and 14B. FIG. 14D is a regular color image (shown in gray scale) of the bowel with room light illumination. FIG. 14E is a blood flow and perfusion image of the bowel in accordance with some embodiments of the present inventive concept.

Referring now to FIGS. 15A to 19B, details with respect to real time image quality test protocols will be discussed. Real time image quality test protocols are developed based on customized algorithms using image registration and image metadata to examine the following issues during a clinical imaging procedure:

Movement of target: FIGS. 15A and 15B illustrate images of a stationary hand (15A) and a moving hand (15B) detected by a customized image registration algorithm.

Movement of a field of view or the Camera: FIGS. 16A and 16B illustrate imaging of a hand image captured by stationary camera (16A) and a hand captured by moving camera (16B) detected by customized image registration algorithm.

Figure 17A:
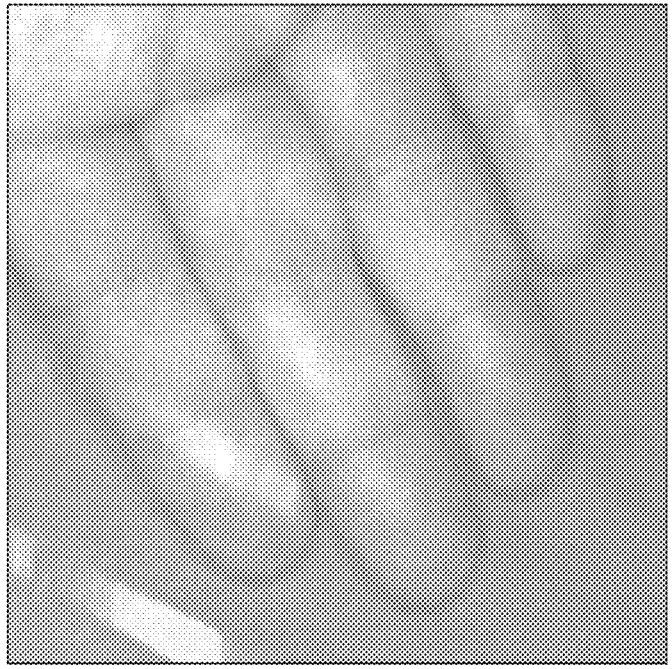
Figure 17B:
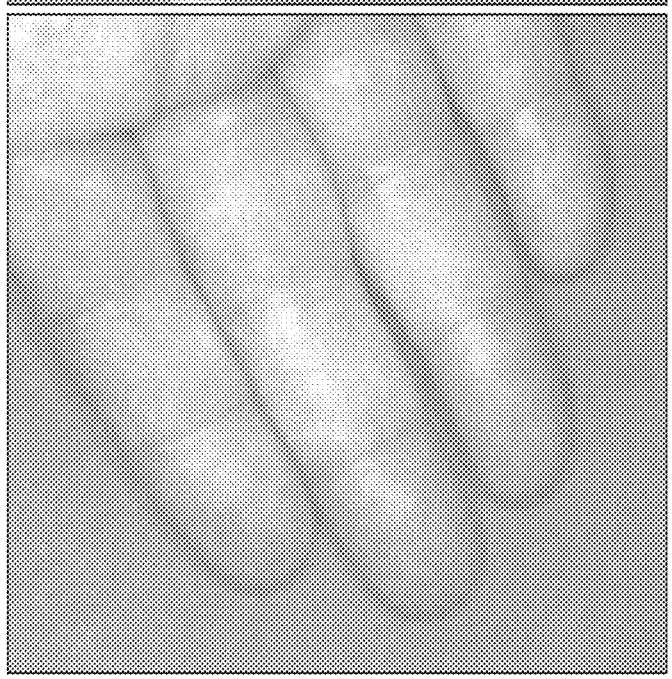

Blocked field of view: FIGS. 17A and 17B illustrate an image of a hand (17A) and an image of a hand that is partially blocked by a twister (17B) and this blocked field of view is detected by a customized image registration algorithm.

Intrusion of headlight of surgeon/physician: FIGS. 18A and 18B illustrate an image of a hand (18A) and an image of a hand with a head light shining on it (18B) and this extra light within the FOV is detected by a customized algorithm using metadata in the image.

Ambient light condition: FIGS. 19A and 19B illustrate an image of a hand with a room light off (19A) and an image of a hand image with the room light on (19B) and this is detected by customized algorithm using metadata in the image.

The goal of this process is to reduce the likelihood, or possibly eliminate, low quality images caused by incorrect image acquisition to improve the visualization and increase accuracy of the quantification of the blood flow and perfusion imaging in accordance with some embodiments of the present inventive concept.

As discussed above, the data obtained using the imaging methods discussed above can only be used to derive distribution of blood flow speed u. In clinics, the information on distribution of blood flow rate given by the product of blood flow velocity u and the cross section area of blood vessel A is needed. To obtain the distribution of u(r) where r is the three dimensional coordinate, the Navier-Stokes equation has to be solved, which is given by Equations (9) and (10) set out below:

$$\rho \cdot \left( \frac{\partial u}{\partial t} + u \nabla \cdot u \right) = -\nabla p + \mu \cdot \nabla^2 u + F \quad \text{Eqn. (9)}$$

$$\frac{\partial \rho}{\partial t} + \nabla \cdot (\rho u) = 0 \quad \text{Eqn. (10)}$$

where $\rho$ is the density (kg/m$^3$), u is the flow velocity vector (m/s), p is the pressure (N/m$^2$ or Pascal), F is the volume force vector (N/m$^3$) and $\mu$ is the viscosity. Solving the Navier-Stokes equations produces a velocity field, i.e. a distribution of fluid velocity in space and time. Once this velocity field is obtained, other quantities of interest, such as flow rate and drag force, can be calculated. These calculated quantities can be compared to the experimental data obtained using the methods discussed above to validate the data.

Computational procedures for a non-invasive measurement of blood flow rate distribution in principal vessels in tissues/organs will now be discussed with respect to some embodiments of the present inventive concept. Procedures begin by illuminating a tissue region of interest with a coherent light source, such as a laser with sufficiently long wavelength for relatively large penetration depth between, for example, 550 nm to about 1100 nm as the second wavelength. Using methods discussed above, scattered light at the second wavelength is acquired to determine spatial distribution of blood flow speed in the principal vessels and perfusion distribution in tissue in the region of interest. A velocity field of u(r) for the region of interest is calculated numerically. In some embodiments, the velocity field is calculated using Equations (9) and (10) set out above. Blood flow speed in the region of interest based on the calculated velocity field is calculated. The calculated blood flow speed in the region of interest is compared to the blood flow speed determined using the acquired image data at the second wavelength from the region of interest to verify results.

In the drawings and specification, there have been disclosed example embodiments of the inventive concept. Although specific terms are employed, they are used in a generic and descriptive sense only and not for purposes of limitation, the scope of the inventive concept being defined by the following claims.

That which is claimed is:

1. A multispectral imaging system, the system comprising:
   a first light source, the first light source being one of coherent, non-coherent and partially coherent, the first light source having a first wavelength configured to produce a non-coherent illumination to image a sample;
   a second coherent light source, different from the first light source, having a second wavelength, different from the first wavelength, configured to image the sample simultaneously with the first light source;
   a camera configured to simultaneously receive information related to the first and second light sources from the sample, wherein light at the first wavelength is configured to image a surface of the sample into the camera and light at the second wavelength is configured to penetrate the sample and provide information related to the penetrated sample to the camera; and
   a processor configured to combine the received information related to the first and second light sources and generate a synthesized image of the sample comprising surface anatomical structure and sub-surface physiology of blood flow and perfusion of the sample in terms of a blood flow rate distribution.

2. The system of claim 1, wherein the first and second wavelengths have different wavelengths in a range from 350 nm to 1100 nm.

3. The system of claim 2, wherein the first wavelength is in one of an ultraviolet (UV) and a visible spectrum and the second wavelength is in one of a visible and near infrared spectrum.

4. The system of claim 1, wherein the sample is an in vivo sample and comprises at least one of tissue and an organ.

5. The system of claim 1, wherein the processor is further configured to reconstruct a color image depicting a surface anatomical view of the sample using at least one monochromatic camera in real time and direct a display in communication with the processor to display the color image simultaneously with a sub-surface blood flow and perfusion distribution map in real time.

6. The system of claim 1, wherein the processor is further configured to use coherent light of wavelength in one of a visible and a near infrared (NIR) spectrum to replace a red color spectrum to provide deeper sub-surface tissue information in the synthesized image.

7. The system of claim 1, wherein an output of the system provides a general sub-surface blood flow speed distribution map and surface anatomical structure simultaneously in real time.

8. The system of claim 1, wherein the processor is further configured to calculate sub-surface blood flow rate or rates from a measured distribution of velocity in a field of view of the sample for the sub-surface blood flow rate distribution.

9. The system of claim 1, wherein the processor is further configured to separate motion of the sample determined from surface anatomical structure from motion of sub-surface blood flow and perfusion in the synthesized image.

10. The system of claim 1, wherein the processor is further configured to remove motion artifacts of the imaged sample caused by sample movement in order to improve accuracy of quantification of sub-surface blood flow and perfusion, wherein the blood flood flow and perfusion of the sample relative to a host tissue/organ including blood vessels is calculated using the following equation:

$$v_{12}(r)=v_{13}(r)+v_{32}(r)=v_{13}(r)-v_{23}(r),$$

wherein $v_{12}(r)$ is the blood flood flow and perfusion of the sample relative to the host tissue/organ; $v_{13}(r)$ is a velocity distribution of the sample relative to the camera; $v_{32}(r)$ is a velocity distribution of the camera relative to the host tissue/organ; and $v_{23}(r)$ is a velocity distribution of the host tissue/organ relative to the camera.

11. The system of claim 1, wherein the processor is further configured to remove motion artifact of the imaged sample caused by movement of an imaging platform holding the camera and/or the camera in order to improve accuracy of quantification of blood flow and perfusion.

12. The system of claim 1, wherein the first light source comprises a non-coherent light source or a laser with coherent length of laser illumination significantly reduced, and wherein the processor is further configured to improve quantification accuracy in coherent illumination based on blood flow and perfusion technologies by removing motion artifacts of the imaged sample.

13. The system of claim 12, wherein the multi-spectral imaging system is configured as a laser-based blood flow and perfusion measuring system comprising one or more of laser speckle imaging (LSI), laser Doppler imaging (LDI), Florescence imaging, reflectance imaging and/or LSI plus Fluorescence imaging.

14. The system of claim 12, wherein the processor is further configured to improve quantification accuracy in laser-based blood flow and perfusion measuring technologies by removing static background noise caused by a difference of optical characteristics of an inhomogeneous scattering media.

15. The system of claim 1, wherein the processor is further configured to direct a display in communication with the processor to display the synthesized image with the surface anatomical structure and the physiology of sub-surface blood flow and perfusion of the sample simultaneously in real time.

16. The system of claim 1, wherein the camera is further configured to receive information related to more than two wavelengths, and wherein each of the more than two wavelengths provides data related to the surface anatomical structure and sub-surface blood flow physiology at corresponding different depths in the sample.

17. The system of claim 1, wherein the first wavelength is configured to image the surface and extend from between 300 nm to 600 nm into the sample and the second wavelength is configured to penetrate the sample from between 500 nm to 1500 nm.

18. The system of claim 1, wherein the system is configured to image a macro field of view (FOV).

19. The system of claim 1, wherein the camera comprises a camera including one of split sensors or multiple sensors, and wherein the one of the split sensors and multiple sensors are configured to simultaneously receive multiple wavelength images as the received information related to the first and second light sources.

20. The system of claim 1, wherein a velocity of the sample is calculated using the following equation:

$$v(i, j) = v_0 + \frac{a}{C(i, j)^2}$$

where $v(i,j)$ is the velocity of the sample, $v_0$ is an added term to account for background noise; a is a constant related to imaging parameters, laser parameters, and time/spatial smoothing parameters for obtaining c and reflects optical characteristics of the sample; c is laser speckle contrast; and i and j are row and column pixel indexes, respectively.

21. A method for multispectral imaging in a multispectral imaging system, the method comprising:

simultaneously imaging a sample using a first light source having a first wavelength configured to produce a non-coherent illumination and a second coherent light source, different from the first light source, having a second wavelength, different from the first wavelength;

receiving information related to the first and second light sources simultaneously from the sample at a camera, wherein light at the first wavelength is configured to reflect off a surface of the sample into the camera and light at the second wavelength is configured to penetrate the sample and provide information related to the penetrated sample to the camera; and combining the received information related to the first and second light sources to generate a synthesized image of the sample comprising surface anatomical structure and sub-surface physiology of blood flow and perfusion of the sample in terms of a blood flow rate distribution, wherein at least one of the imaging, receiving and combining are performed by at least one processor.

22. The method of claim 21, wherein the first wavelength is in one of an ultraviolet (UV) and a visible spectrum and the second wavelength is in one of a visible and a near infrared spectrum.

23. A computer program product for multispectral imaging in a multispectral imaging system, the computer program product comprising:

a non-transitory computer readable storage medium having computer readable program code embodied in the medium, the computer readable program code comprising:

computer readable program code to direct a first light source to transmit light onto a sample, the first light source having a first wavelength configured to produce a non-coherent illumination and direct a second light source to transmit light into the sample, the second light source being different from the first light source and having a second wavelength configured to produce coherent illumination, different from the first wavelength, wherein light at the first wavelength is configured to reflect off a surface of the sample into a camera and provide information regarding the sample to the camera and light at the second wavelength is configured to penetrate the sample and provide information related to the penetrated sample to the camera simultaneously with the information from the first wavelength; and computer readable program code to combine the information related to the first and second light sources received simultaneously by the camera to generate a synthesized image of the sample comprising surface anatomical structure and physiology of sub-surface blood flow and perfusion of the sample in terms of blood flow rate distribution.

* * * * *

UNITED STATES PATENT AND TRADEMARK OFFICE
CERTIFICATE OF CORRECTION

PATENT NO. : 10,058,256 B2
APPLICATION NO. : 15/054830
DATED : August 28, 2018
INVENTOR(S) : Chen et al.

It is certified that error appears in the above-identified patent and that said Letters Patent is hereby corrected as shown below:

In the Specification

Column 8, Line 32: delete "43 nm" and insert -- 430 nm --

Column 11, Line 50: delete "(ti,j)" and insert -- (i,j) --

Column 11, Line 57: delete "450-495" and insert -- 450~495 --

In the Claims

Column 20, Claim 20, Line 8: delete "obtaining c" and insert -- obtaining C --

Column 20, Claim 20, Line 9: delete "sample; c" and insert -- sample; C --

Signed and Sealed this
Fourth Day of December, 2018

Andrei Iancu
*Director of the United States Patent and Trademark Office*